(12) United States Patent
Noda et al.

(10) Patent No.: US 8,106,366 B2
(45) Date of Patent: Jan. 31, 2012

(54) ION BEAM CONTROL APPARATUS AND METHOD

(75) Inventors: Akira Noda, Uji (JP); Toshiyuki Shirai, Uji (JP); Masahiro Ikegami, Uji (JP); Shu Nakamura, Uji (JP); Hiroyuki Daido, Kizukawa (JP); Kouji Noda, Chiba (JP)

(73) Assignees: Kyoto University (JP); National Institute of Radiological Sciences (JP)

( * ) Notice: Subject to any disclaimer, the term of this patent is extended or adjusted under 35 U.S.C. 154(b) by 176 days.

(21) Appl. No.: 12/600,540

(22) PCT Filed: May 20, 2008

(86) PCT No.: PCT/JP2008/059202
§ 371 (c)(1),
(2), (4) Date: Feb. 5, 2010

(87) PCT Pub. No.: WO2008/143242
PCT Pub. Date: Nov. 27, 2008

(65) Prior Publication Data
US 2010/0133445 A1    Jun. 3, 2010

(30) Foreign Application Priority Data
May 21, 2007  (JP) .................................. 2007-134132

(51) Int. Cl.
*H01J 27/02*    (2006.01)
*H01J 3/14*    (2006.01)
*H01J 3/08*    (2006.01)

(52) U.S. Cl. ................ 250/396 R; 250/423 R; 250/424; 250/503.1; 250/505.1

(58) Field of Classification Search ............... 250/396 R, 250/423 R, 424, 503.1, 505.1
See application file for complete search history.

(56) References Cited

U.S. PATENT DOCUMENTS

| 7,303,982 B2 * | 12/2007 | Collins et al. ................. 438/514 |
| 7,700,465 B2 * | 4/2010 | Collins et al. ................. 438/513 |
| 2002/0180365 A1 | 12/2002 | Okamura et al. |

FOREIGN PATENT DOCUMENTS

| EP | 0233083 | 8/1987 |
| JP | 63225459 | 9/1988 |
| JP | 11-174198 | 7/1999 |

OTHER PUBLICATIONS

A. Noda et al., Beam Science and Technology, vol. 6, 2001, pp. 21-23.
A. Noda et al., Laser Physics 2006, vol. 16, No. 4, pp. 647-653.

(Continued)

*Primary Examiner* — Nikita Wells
(74) *Attorney, Agent, or Firm* — Gerald E. Hespos; Michael J. Porco

(57) ABSTRACT

Provided are an ion beam control apparatus and a control method for controlling an ion beam energy expansion level and an ion beam size in a radial direction. An ion beam control apparatus Sa is provided with an ion beam generating unit 2, and an ion beam control unit 1a in which a generated ion beam (IB) is input and controlled to be output with the prescribed level of energy expansion and the prescribed diameter in the radial direction. In the ion beam control unit 1a, phase rotation by a radio frequency electric field that increases existing probability with the prescribed level of energy is at least used.

14 Claims, 14 Drawing Sheets

OTHER PUBLICATIONS

Noda et al.: "High Quality Laser-Produced Proton Beam Generation by Phase Rotation" International Journal of Modern Physics B, World Scientific, Singapore, SG, vol. 21, No. 3-4, Feb. 10, 2007, pp. 319-330.

Luo et al.: "Practicle Selection and Beam Collimation System for Laser-Accelerated Proton Beam Therapy" Medical Physics, AIP, Melville, NY, US, vol. 32, No. 3, Mar. 2, 2005 pp. 794-806.

Akira Noda: Internet Citation, Nov. 16, 2005, pp. 28pp, XP007916737.

Akira Noda et al., "5.13 Iso Kaiten ni yoru Laser Seisei Yoshi no Energy Peak Keisei", JAEA-Conf, Mar. 2007, 2007-001, pp. 189-192.

Shu Nakamura, "Iso Kaiten ni yoru Kokyodo Laser Kigen Ion no Energy Tanshokuka", [online], [retrieval date Jun. 5, 2008], The Japanese Beam Physics Club, Nov. 17, 2006, Internet, <URL:http://beam.spring8.or.jp/localfs/beam_Web/Proceedings/Proceedings_2006/program.html>.

Akira Noda, "Laser Ion Beam no RF Iso Kaiten Kudo ni yoru Seigyo", [online], [retrieval date Jun. 5, 2008], The Japanese Beam Physics Club, Nov. 16, 2005, Internet, <URL:http://beam.spring8.or.jp/localfs/beam_Web/Proceedings/Proceedings_2005/program.html>.

* cited by examiner

IN THE CASE OF 50kV 0.866~0.877 [MeV]

0.89~0.90 [MeV]

IN THE CASE OF 80kV 0.65～0.68 [MeV]

0.68～0.70 [MeV]

0.70～0.72 [MeV]

0.83～0.86 [MeV]

0.86～0.89 [MeV]

0.89～0.92 [MeV]

IN THE CASE OF 90kV 0.82～0.84 [MeV]

0.92～0.94 [MeV]

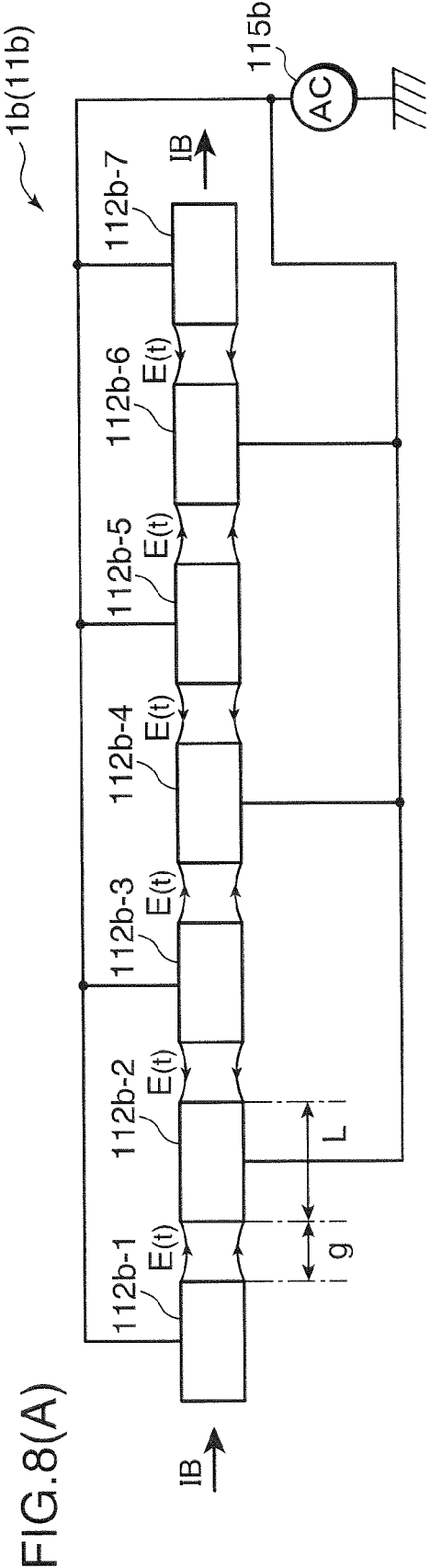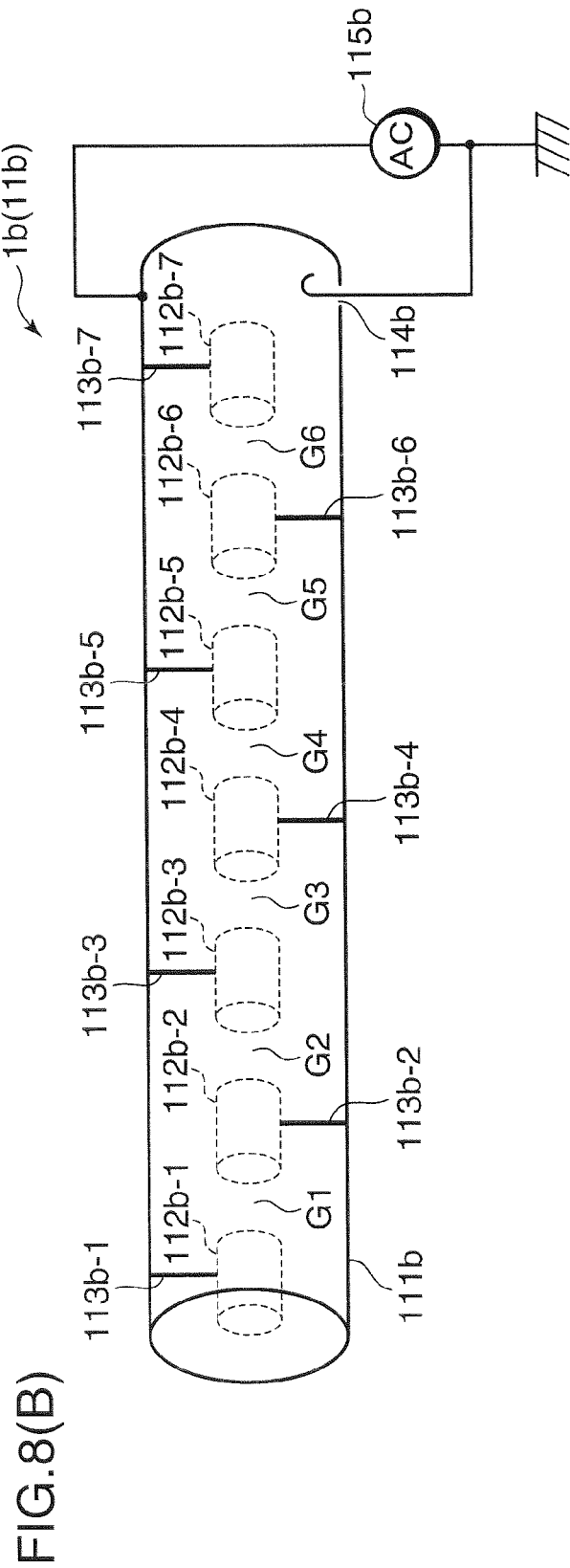

IN THE CASE WHERE PHASES BETWEEN ADJACENT GAPS ARE OFF 180° OUT OF PHASE

WITH PHASE ROTATION

WITHOUT PHASE ROTATION

IN THE CASE WHERE PHASE OF EACH GAP IS SAME

WITHOUT PHASE ROTATION

WITH PHASE ROTATION

FIG.13(A)
FIG.13(B)
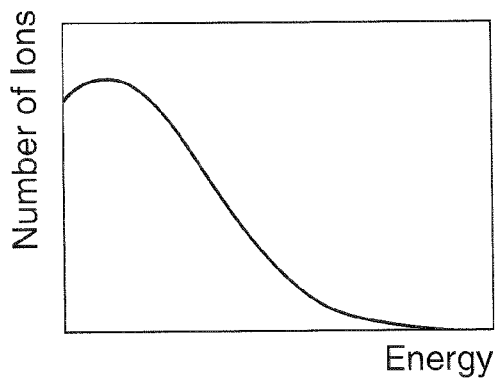
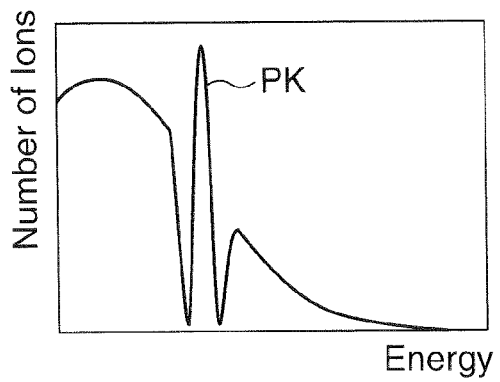
FIG.13(C)
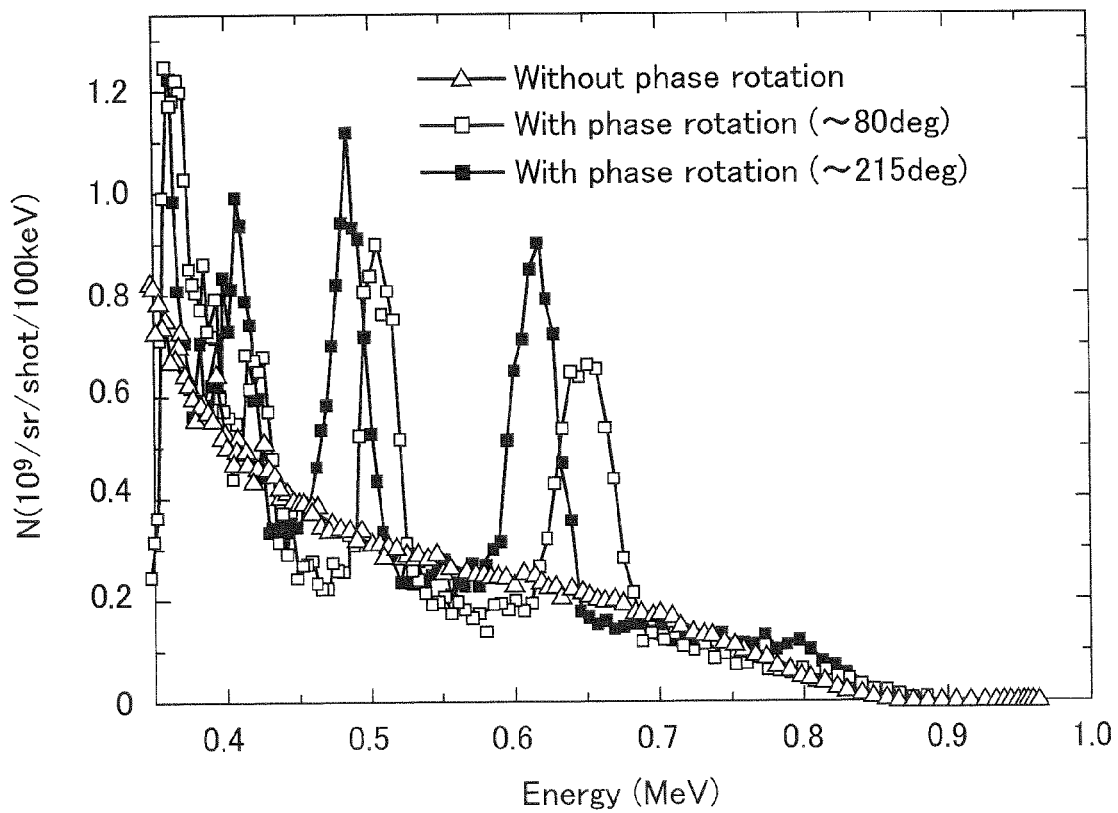

ION BEAM CONTROL APPARATUS AND METHOD

BACKGROUND OF THE INVENTION

1. Field of the Invention

The present invention is related to an ion beam control apparatus and its control method capable of controlling ion beams.

2. Description of the Related Art

FIG. 12 is a diagram showing the configuration of a conventional ion beam control apparatus. FIG. 13 is a diagram showing the intensity distribution in relation to the ion beam energy. FIG. 13(A) is a view showing a frame format of the intensity distribution in relation to the energy of ion beams generated based on the irradiation of a pulse laser, FIG. 13(B) is a view showing a frame format of the intensity distribution in relation to the energy of ion beams controlled with the ion beam control apparatus, and FIG. 13(C) is a diagram showing the test results thereof. The horizontal axis of FIG. 13(A) to FIG. 13(C) shows the energy, and the vertical axis thereof shows the ion beam intensity; that is, the existing probability of ions. The unit of the horizontal axis of FIG. 13(C) is MeV, and the unit of the vertical axis thereof is $10^9$/sr/shot/100 keV.

As shown in FIG. 12, when a pulsed laser beam (pulse laser beam) PL is irradiated onto a solid thin film MF, the solid thin film MF will be heated by the pulse laser beam PL, and an ion beam IB is created thereby. With respect to the intensity distribution (energy spectrum) in relation to the energy of the ion beam IB, as shown in FIG. 13(A), in parallel with a peak formation of the intensity (existing probability of ions) on the low energy side, the intensity will exponentially decrease together with the increase of energy. Thus, if the user wishes to use an ion beam IB having a prescribed energy, there are cases where the prescribed intensity cannot be obtained, and there is an inconvenience upon using the ion beam IB.

Thus, proposed is a method of using the ion beam control apparatus 1000 shown in FIG. 12 to control the intensity distribution in relation to the energy of the ion beam IB using the phase rotation by a radio frequency electric field (A. Noda et al., Beam Science of Technology, Vol. 6, 2001. PP 21-23 and A. Noda et al., Laser Physics 2006, Vol. 16, No. 4, PP 647-653). The ion beam control apparatus 1000 shown in FIG. 12 comprises a cylindrical case 1001, and a radio frequency electric field generation unit 1002 (1002-1 to 1002-3) for generating a radio frequency electric field E(t). The radio frequency electric field generation unit 1002 comprises three cylindrical first to third electric field generation components 1002-1 to 1002-3 arranged so the ion beam IB passes therethrough and the radio frequency electric field E(t) affects the ion beam IB. The first to third electric field generation components 1002-1 to 1002-3 are respectively arranged continuously from one side face to the other side face of the case 1001 so that they will mutually have prescribed spacings, so that the central axes will mutually coincide, and so that the central axis of the first to third electric field components 1002-1 to 1002-3 and the central axis of the case 1001 will mutually become orthogonal. More specifically, the first electric field generation component 1002-1 is disposed on one side face of the case 1001 so as to penetrate the side face of the case 1001, and so that the central axis of the first electric field generation component 1002-1 and the central axis of the case 1001 will mutually become orthogonal. The second electric field generation component 1002-2 is disposed in the case 1001 by being supported by a support member 1003 that is suspended from the inner face of the top cover of the case 1001 at a prescribed spacing from the first electric field generation component 1002-1 and so that the central axis of the first electric field generation component 1002-1 and the central axis of the second electric field generation component 1002-2 will mutually coincide. The third electric field generation component 1002-3 is disposed on the other side face facing the one side face of the case 1001 at a prescribed spacing from the second electric field generation component 1002-2 and so that the central axis of the second electric field generation component 1002-2 and the central axis of the third electric field generation component 1002-3 will mutually coincide, and so as to penetrate the side face of the case 1001. A radio frequency (RF) AC voltage is applied to the case 1001 and the radio frequency electric field generation unit 1002 with an AC source not shown. Consequently, a radio frequency electric field E(t) will be generated in the first space (first gap) G1 between the first electric field generation component 1002-1 and the second electric field generation component 1002-2, and the second space (second gap) G2 between the second electric field generation component 1002-2 and the third electric field generation member 1002-3, respectively.

With the ion beam control apparatus 1000 configured as described above, a peak PK of the intensity can be generated in a given energy of the ion beam IB using the phase rotation by the radio frequency electric field E(t) as shown in FIG. 13(B). This has been confirmed based on testing as shown in FIG. 13(C). Δ of FIG. 13(C) shows the test results in a case without phase rotation, □ shows the test results in a case where the phase rotation is applied with a relative phase between the pulse laser and an RF electric field of 80 degrees, and ■ shows the test results in a case where the phase rotation is applied with a relative phase between the pulse laser and an RF electric field of 215 degrees. In the case without phase rotation, together with the increase of energy, the intensity is decreasing gradually. However, in cases with phase rotation of 80 degrees or 215 degrees, plural intensity peaks are formed.

This can be explained as follows. FIG. 14 is a diagram explaining the phase rotation of ion beams. The horizontal axis of FIG. 14 shows the phase of the radio frequency electric field, and the vertical axis thereof shows the strength of the radio frequency electric field E(t).

The ion beam IB generated with the pulse laser beam PL is configured, as shown in FIG. 13(A), plural ions having various values of energy, and high energy ions will reach the first gap G1 faster than the low energy ions. Thus, as shown in FIG. 14, with the ion Pa having the reference energy to form an intensity peak, the ion Pb having an energy that is higher than the ion Pa will reach the first gap G1 faster than the ion Pa, and the ion Pc having an energy that is lower than the ion Pa will reach the first gap G1 later than the ion Pa. Thus, if the radio frequency electric field E(t) is caused to affect the ion beam so as to accelerate the ion Pb having an energy that is higher than the ion Pa in the amount of energy that is smaller than the ion Pa, and accelerate the ion Pc having an energy that is lower than the ion Pa in the amount of energy that is greater than the ion Pa, and the distance L between the first gap G1 and the second gap G2 is set so that the radio frequency electric field E(t) affects the ion Pa with the same phase in the first gap G1 and the second gap G2, the energy of the ion Pb and the energy of the ion Pc will respectively approach the energy of the ion Pa. Consequently, the intensity peak PK can be formed at the energy of the ion Pa. The compression of the energy expansion of the ion beam IB using the radio frequency electric field E(t) is referred to as the phase rotation by the radio frequency electric field.

On the other hand, as an application example of this kind of ion beam IB, for instance, there are the surface treatment technology of performing surface modification by injecting trace amounts of elements as a result of irradiating the ion beam IB, and the particle radiation therapy that causes damage to the cancer cells by irradiating the ion beam IB. Generally speaking, with the radiation of X rays, γ rays and so on and neutron radiation, the dose will become maximum at a site that is relatively shallow in the body, and the dose will gradually decrease. Thus, with radiation of X rays, γ rays and so on and neutron radiation, damage will also be inflicted on the normal cells around the cancer. Meanwhile, with a particle beam such as a proton beam or a carbon ion beam, the dose will be relatively low on the body surface, and becomes a maximum dose (Bragg peak) at the deepest site, and the dose will be nearly zero at any deeper site. Thus, with the particle beam, if the Bragg peak is irradiated to match the affected area of the cancer, it is possible to damage the cancer cells without much affecting the normal cells around the depth direction. Conventionally, in order to perform this kind of particle radiation therapy, a relatively large accelerator such as a cyclotron or a synchrotron was required.

With the foregoing ion beam control apparatus 1000, although it is possible to control the formation of the intensity peak PK to a prescribed energy, the ion beam IB will diverge in the moving radius direction (perpendicular direction in relation to the traveling direction). Moreover, since an electrostatic breakdown will occur if high voltage of a certain level or higher is applied to the first to third electric field generation components 1002-1 to 1002-3, the voltage that can be applied to the first to third electric field generation components 1002-1 to 1002-3 will be limited. Consequently, the phase rotation of the high energy ion beam IB cannot be performed.

In particular, when considering the use of the ion beam IB, it is desirable to control (convergence in the moving radius direction) of the energy expansion level in the ion beam IB and the energy expansion level in the moving radius direction, and the realization of high energy.

SUMMARY OF THE INVENTION

The present invention was devised in view of the foregoing circumstances, and an object of this invention is to provide an ion beam control apparatus and an ion beam control method capable of controlling the energy expansion level and the ion beam size in the radial direction.

With the ion beam control apparatus and the ion beam control method according to the present invention, upon controlling the ion beam, the phase rotation by the radio frequency electric field that increases the existing probability with the prescribed level of energy is at least used so that the ion beam is input, and the ion beam is output at a prescribed diameter in the radial direction with a prescribed level of energy spread. Accordingly, the intensity peak can be formed to the intended energy using the phase rotation by the radio frequency electric field, and, as a result of cutting out this intensity peak, it is possible to control the energy spread level and the ion beam size in the radial direction.

BRIEF DESCRIPTION OF THE DRAWINGS

FIG. 8 is a diagram showing the configuration of an ion beam control unit according to the second embodiment.

FIG. 13 is a diagram showing the intensity distribution in relation to ion beam energy.

DETAILED DESCRIPTION OF THE PREFERRED EMBODIMENTS

Embodiments of the present invention are now explained with reference to the drawings. Components that are given the same reference number in the respective diagrams show that they are the same components, and the explanation thereof is omitted.

The ion beam control apparatus according to one embodiment of the present invention is generally configured as follows; specifically, it includes an open aperture at a central part, wherein at least a pair of electrodes arranged to face each other is provided, an ion beam is input from a perpendicular direction of the open aperture, and, in a phase where an inclined part of a radio frequency electric field intensity accelerating or decelerating the ion beam to the pair of electrodes, the radio frequency is applied so as to cause the energy of the ion beam to focus on a specific energy and accelerate. With this ion beam control apparatus, at least another pair of electrodes arranged to face each other is provided to the pair of electrodes, and an ion beam is converged on the other pair of electrodes by an electric field component facing a beam center direction by applying radio frequency in a direction of accelerating the ions (main electric field vector is the same direction as the traveling direction of the ions) between an intermediate part of the other pair of electrodes and an electrode of an ion input side. Preferably, an ion beam is converged by an electric field component facing a beam center direction by applying radio frequency in a direction of decelerating the ions (main electric field vector is the reverse direction as the traveling direction of the ions) between the intermediate part of the other pair of electrodes and an electrode of an ion output side. More preferably, an ion beam is converged by an electric field component facing a beam center direction by applying radio frequency in a direction of accelerating the ions (main electric field vector is the same direction as the traveling direction of the ions) between an intermediate part of the pair of electrodes and an electrode of an ion input side, and, after the ion beam passes through the intermediate part of the electrode, an ion beam is converged by an electric field component facing a beam center direction by applying radio frequency in a direction of decelerating the ions (main electric field vector is the reverse direction as the traveling direction of the ions) between the intermediate part of the pair of electrodes and an electrode of an ion output side. More preferably, the pair of electrodes and the other pair of electrodes are arranged alternatively in multiple times.

First Embodiment

Figure 1:
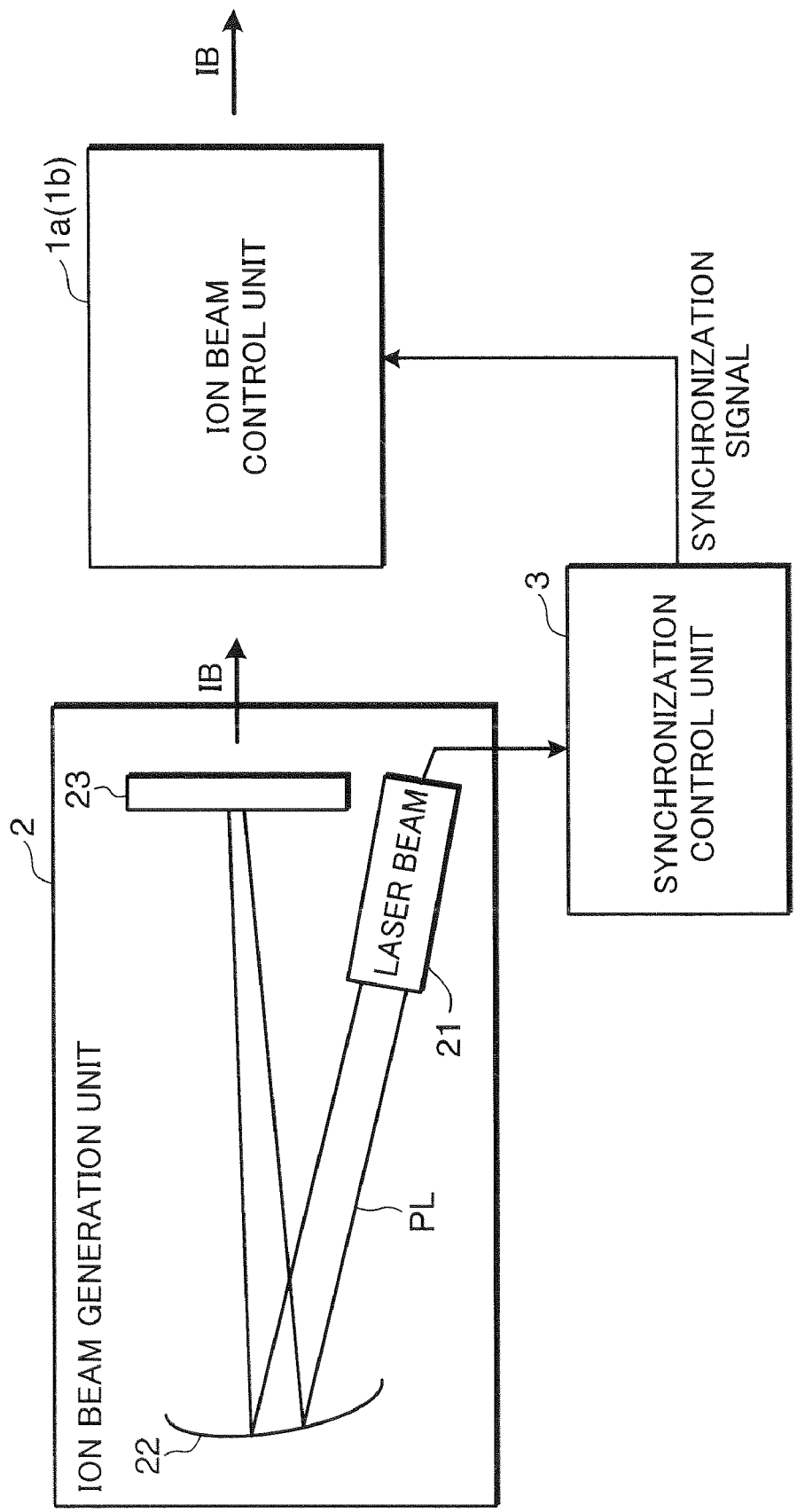
FIG. 1 is a diagram showing the configuration of an ion beam control apparatus according to an embodiment.
Figure 2:
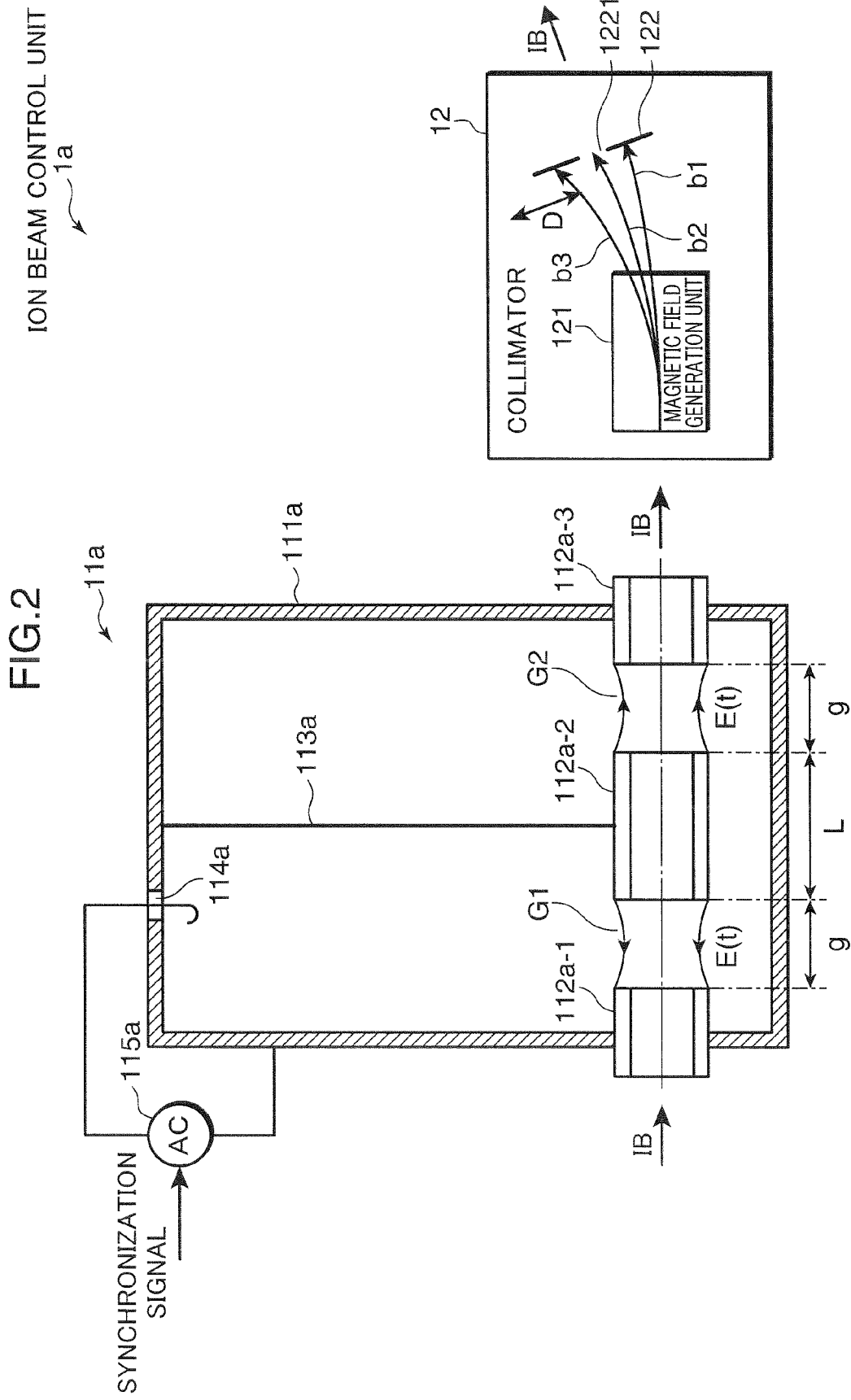
FIG. 2 is a diagram showing the configuration of an ion beam control unit according to the first embodiment.

FIG. 1 is a diagram showing the configuration of an ion beam control apparatus according to an embodiment. FIG. 2 is a diagram showing the configuration of an ion beam control unit according to the first embodiment.

In FIG. 1 and FIG. 2, the ion beam control apparatus Sa is an apparatus for controlling the energy expansion level of the ion beam and the size of the ion beam IB in the radial direction (direction that is perpendicular to the traveling direction of the ion beam IB). In this embodiment, this apparatus is configured, for example, from an ion beam control unit 1a for controlling an ion beam by at least using phase rotation by a radio frequency electric field E(t) that increases existing probability with a prescribed level of energy so that the ion beam IB is input, and the ion beam IB is output with a pre-set prescribed level of energy expansion and a pre-set prescribed diameter in a radial direction, an ion beam generation unit 2 for generating an ion beam IB to be input to the ion beam control unit 1a, and a synchronization control unit 3 for controlling the synchronization of the phase of the radio frequency electric field E(t) in the ion beam control unit 1a and the generation timing of the ion beam IB in the ion beam generation unit 2 so that in the radio frequency electric field E(t) the ion beam. IB is input to the center position of the gap G, which is described later, in an ion beam control unit 1 at the timing that the electric field direction is converted in the input direction of the ion beam IB.

In this embodiment, the ion beam control unit 1a comprises, for example, as shown in FIG. 2, a double gap radio frequency resonator 11a to which the ion beam IB is input and including two gaps for performing phase rotation by the radio frequency electric field E(t) so as to increase existing probability with a prescribed level of energy, and a collimator 12 to which the ion beam IB output from the double gap radio frequency resonator 11a is input, and which outputs the input ion beam IB with the prescribed level of energy expansion and the prescribed diameter in the radial direction. In FIG. 2, the double gap radio frequency resonator 11a is shown in a vertical cross section.

In this embodiment, the double gap radio frequency resonator 11a comprises, for example, a cylindrical case 111a, a radio frequency electric field generation unit 112a (112a-1 to 112a-3) for generating the radio frequency electric field E(t), and a radio frequency (RF) AC source 115a.

Incidentally, in this specification, a reference numeral without a suffix is used when collectively referring to components, and a reference numeral with a suffix is used when referring to individual components.

The radio frequency electric field generation unit 112a comprises three cylindrical first to third electric field generation components 112a-1 to 112a-3 arranged so the ion beam IB passes therethrough and the radio frequency electric field E(t) affects the ion beam IB. The first to third electric field generation components 112a-1 to 112a-3 are respectively arranged continuously from one side face to the other side face of the case 111a so that they will be aligned to create a prescribed distance g of space, so that the central axis will mutually coincide, and so that the central axes of the first to third electric field generation components 112a-1 to 112a-3 and the central axis of the case 111a will mutually become orthogonal. More specifically, the first electric field generation component 112a-1 is disposed on one side face of the case 111a so as to penetrate the side face of the case 111a, and so that the central axis of the first electric field generation component 112a-1 and the central axis of the case 111a will mutually become orthogonal. The second electric field generation component 112a-2 is disposed in the case 111a by being supported by a rod-shaped support component 113a that is suspended from the inner face of the top cover of the case 111a at a prescribed distance g from the first electric field generation component 112a-1 and so that the central axis of the first electric field generation component 112a-1 and the central axis of the second electric field generation component 112a-2 will mutually coincide. The third electric field generation component 112a-3 is disposed on the other side face attached to the one side face of the case 111a at a prescribed distance g from the second electric field generation component 112a-2 and so that the central axis of the second electric field generation component 112a-2 and the central axis of the third electric field generation component 112a-3 will mutually coincide, and so as to be attached to the side face of the case 111a. The arrangement position from the top cover of the case 111a in the first to third electric field generation components 112a-1 to 112a-3 is suitably set so that the double gap radio frequency resonator 11a configures a resonator based on the frequency (wavelength) of the radio frequency electric field E(t).

As a result of the radio frequency electric field generation unit 112a being configured as described above, a first space (first gap) G1 is formed between the first electric field generation component 112a-1 and the second electric field generation component 112a-2, and a second space (second gap) G2 is formed between the second electric field generation component 112a-2 and the third electric field generation component 112a-3.

The length L of the second electric field generation component 112-2 is set so that (L+g) becomes equivalent to a value obtained by multiplying the ion velocity having an energy corresponding to the intensity peak to be formed to the odd multiple time of a ½ cycle (half cycle) of the radio frequency electric field E(t). The ion velocity is obtained from the energy of the ions. When the length L of the second electric field generation component 112-2 is set as described above, the ions having the energy corresponding to the intensity peak to be formed will be affected by the electric field E(t) with the same phase from the electric field E(t) of the first gap G1 and the electric field E(t) of the second gap.

The spacing g of the first and second gaps G1, G2 is set to such a value as the phase of the radio frequency electric field E(t) will not considerably change when the ions having the energy corresponding to the intensity peak to be formed are flying in each gap (such a low level where the change in the radio frequency electric field E(t) while the ions are flying will not substantially affect the ion beam), and which enables the application of the required voltage without causing an electric breakdown.

The case 111a, the first to third electric field generation component 112a-1 to 112a-3 and the support component 113a are formed, for example, from a conductive material such as metal (including alloy), and, in this embodiment, for instance, is formed from copper from the perspective of conductive property, easiness of machinability and the like.

With the AC source 115a, one terminal thereof is connected to the case 111a, and the other terminal is disposed in the case 111a via a through-hole 114a that is drilled through the case 111a, and a radio frequency AC voltage is applied thereto. An insulating material is filled in the through-hole 114a, and the other terminal and the case 111a are insulated. A radio frequency electric field E(t) is thereby respectively generated in the first and second gaps G1, G2 off by a half cycle. With the AC source 115a, the phase of the radio frequency electric field E(t) is controlled with a synchronization signal from the synchronization control unit 3.

In this embodiment, the collimator 12 comprises, for example, a magnetic field generation unit 121 for generating a magnetic field and causing the magnetic field to affect the ion beam IB, and a transmission blocking unit 122 formed with a through-hole 1221. The transmission blocking unit 122 is configured to be movable along an approximate perpendicular direction D in relation to the traveling direction of the ion beam IB that was affected by the magnetic field of the magnetic field generation unit 121, and configured so that the diameter of the through-hole 1221 can be changed. The transmission blocking unit 122 is preferably configured from a material of a heavy element, and, for example, is formed from brass from the perspective of easiness of machinability and because it is relatively inexpensive. The collimator 12 is a magnet spectrograph for example. The collimator 12 may also be a magnet spectrometer configured such that the position of the transmission blocking unit 122 is fixed and the strength of the magnetic field can be changed.

Returning to FIG. 1, in this embodiment, the ion beam generation unit 2 is, for example, a laser generation/ion beam generation device that generates an ion beam IB by irradiating a pulsed laser beam (pulse laser beam) PL onto the solid thin film 23, and comprises, for example, a laser beam source 21 for emitting and outputting a pulse laser beam PL, an optical system 22 configured from a parabolic mirror and so on which converges the pulse laser beam PL output from the laser beam source 21 and outputs it to the solid thin film 23, and a solid thin film 23 formed from a solid material formed in a thin film shape. The solid thin film 23 is formed, for example, from a material of titanium, tantalum, polyimide and so on. Preferably, the solid thin film 23 is as thin as possible in order to more favorably generate the ion beam IB.

The ion beam generation unit 2 is disposed so that the distance from the generation point of the ion beam IB (approximate position that the solid thin film 23 is disposed) to the position that the ion beam IB is input to the first electric field generation component 112a-1 of the double gap radio frequency resonator 11a becomes a prescribed length. The temporal expansion of the ion beam IB is extremely short immediately after the generation thereof, and expands according to the flying distance. This prescribed length is set so that the temporal expansion of the ion beam IB will be less than ½ cycle of the radio frequency electric field E(t).

In this embodiment, the synchronization control unit 3 is, for example, a circuit which is notified of the irradiation timing of irradiating the pulse laser beam PL from the laser beam source 21 of the ion beam generation unit 2, and which notifies the synchronization signal to the AC source 115a of the ion beam control unit 1a so that the ion beam IB is input to the ion beam control unit 1a at the timing that the electric field E(t) direction is converted to the input direction of the ion beam IB based on the irradiation timing, and controls the synchronization of the phase of the radio frequency electric field E(t) in the ion beam control unit 1a and the generation timing of the ion beam IB in the ion beam generation unit 2.

Here, the frequency of the radio frequency electric field E(t) is set to an integral multiple of the frequency of the pulse laser beam. As a result of the frequency of the radio frequency electric field E(t) being set as described above, when controlling the phase of the radio frequency electric field E(t) and the entry timing of the ion beam IB generated with the pulse laser beam into the radio frequency electric field E(t), such control can be facilitated. Thus, the synchronization control unit 3 can be configured in a simple manner.

The operation of the ion beam control apparatus Sa is now explained.

Figure 3:
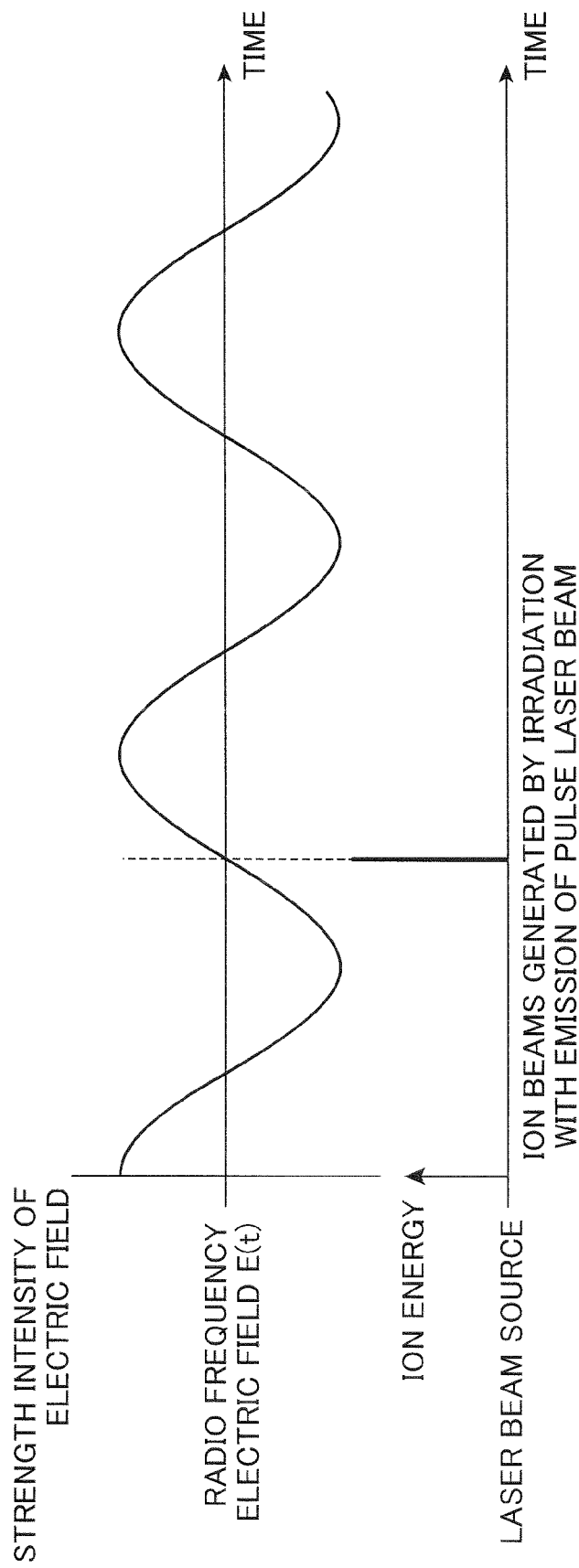
FIG. 3 is a diagram showing the relationship between the irradiation timing of a pulse laser beam and the phase of a radio frequency electric field.
Figure 4:
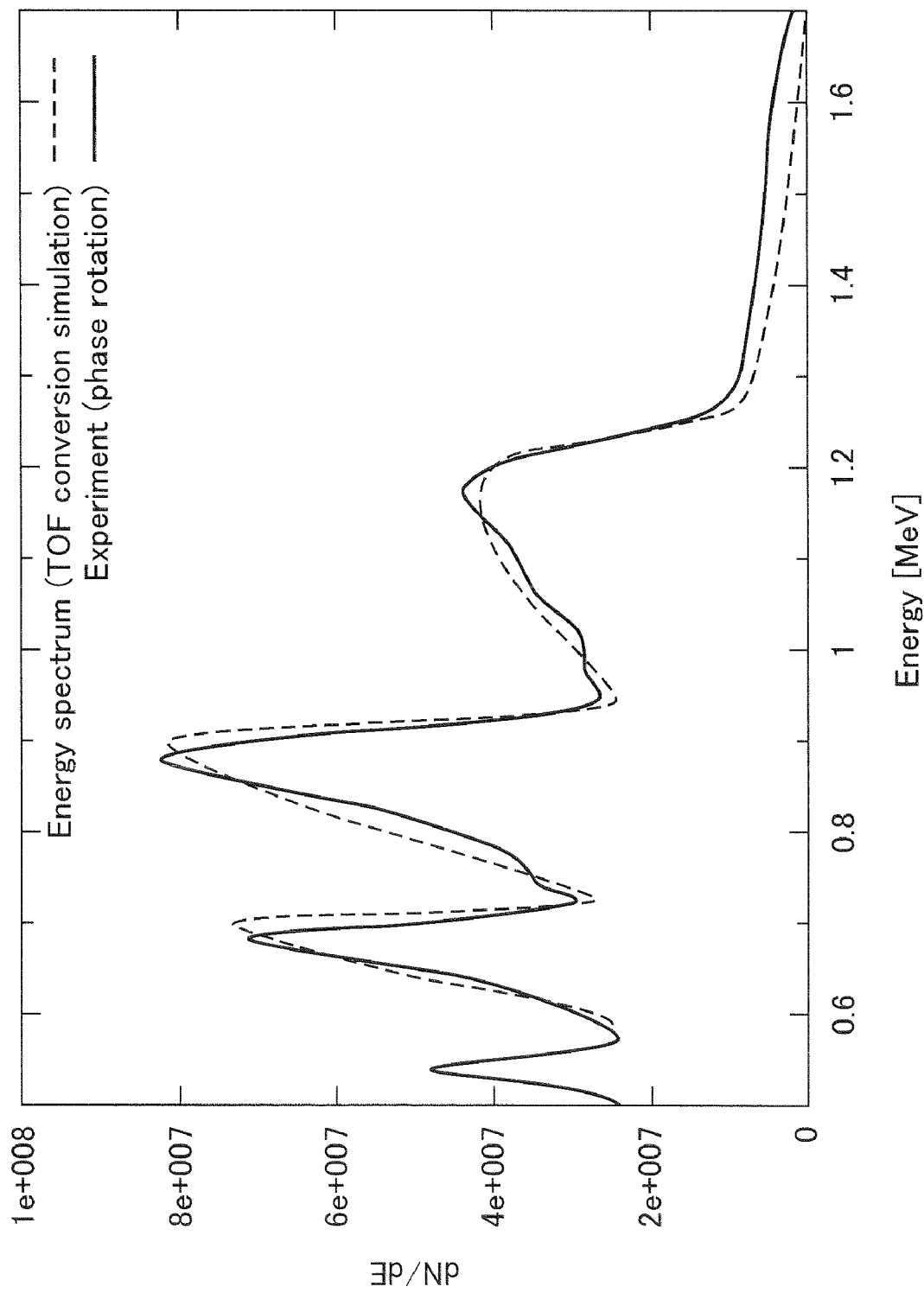
FIG. 4 is a diagram showing the test results and simulation results.
Figure 5A:
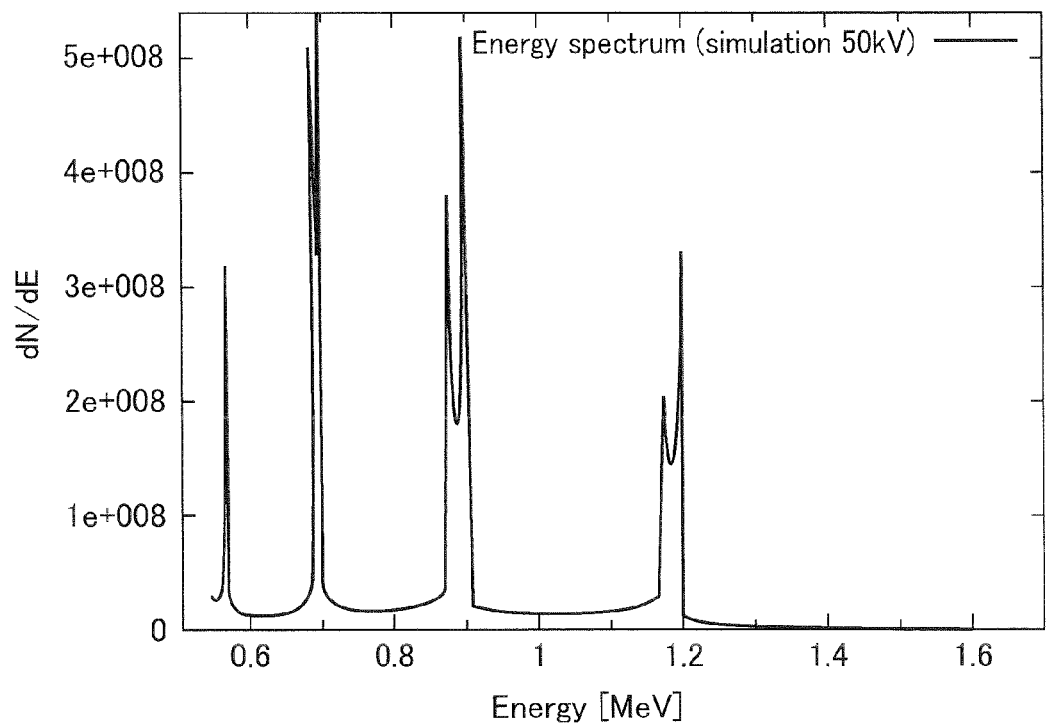
FIG. 5 is a diagram showing the energy spectrum of ion beams controlled with the ion beam control apparatus according to the first embodiment and the ion particle distribution in the radial direction based on prescribed energy (Case 1).
Figure 5B:
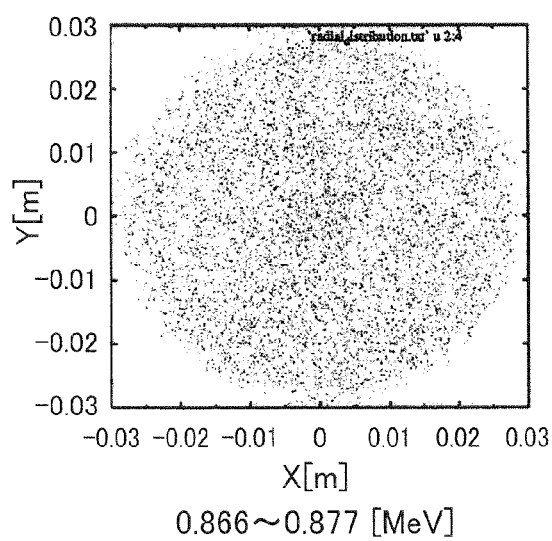
Figure 5C:
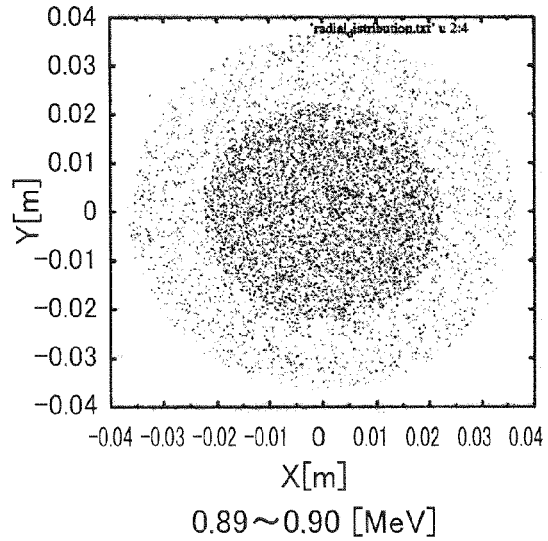
Figure 6A:
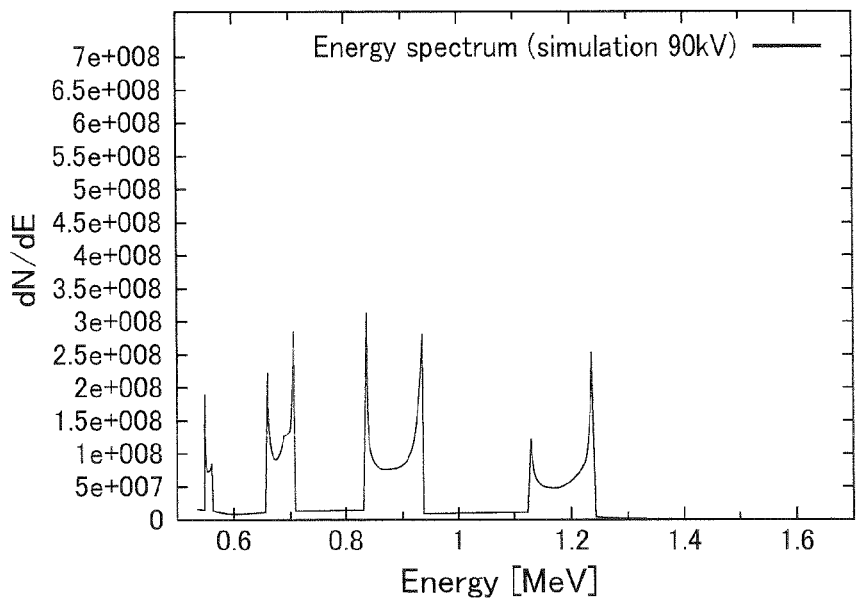
FIG. 6 is a diagram showing the energy spectrum of ion beams controlled with the ion beam control apparatus according to the first embodiment and the ion particle distribution in the radial direction based on prescribed energy (Case 2).
Figure 6B:
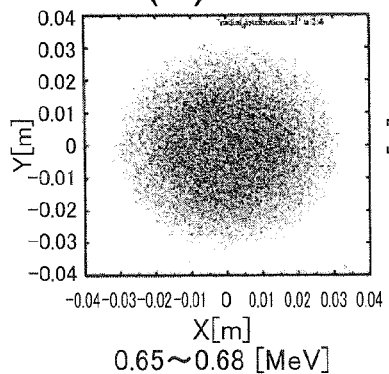
Figure 6C:
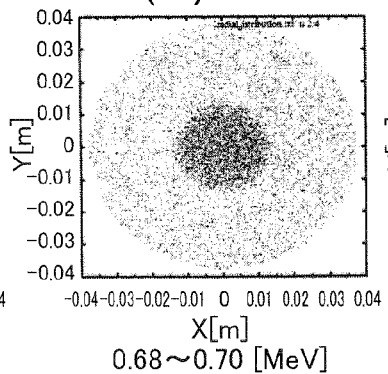
Figure 6D:
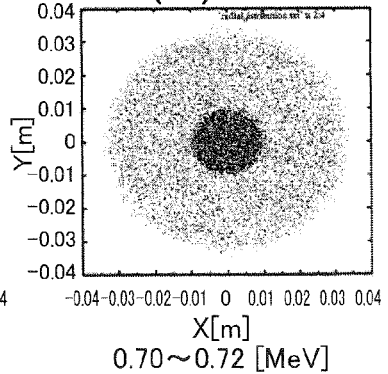
Figure 6E:
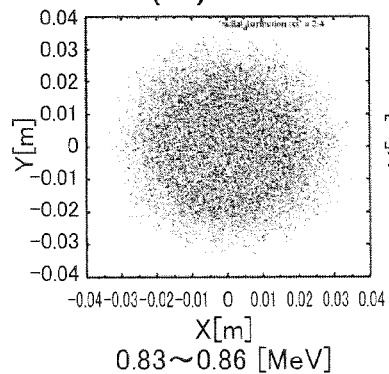
Figure 6F:
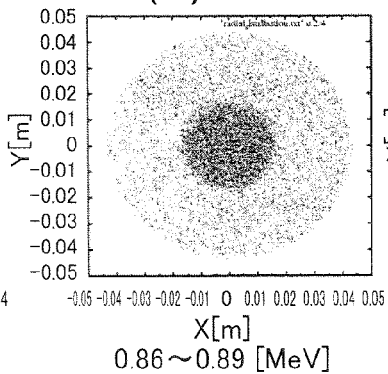
Figure 6G:
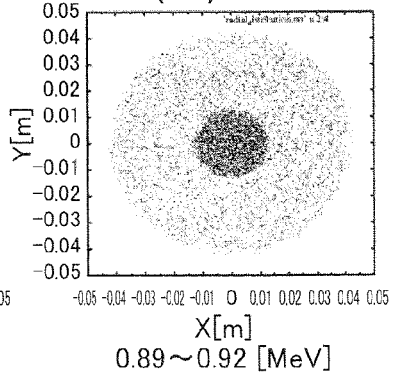
Figure 7A:
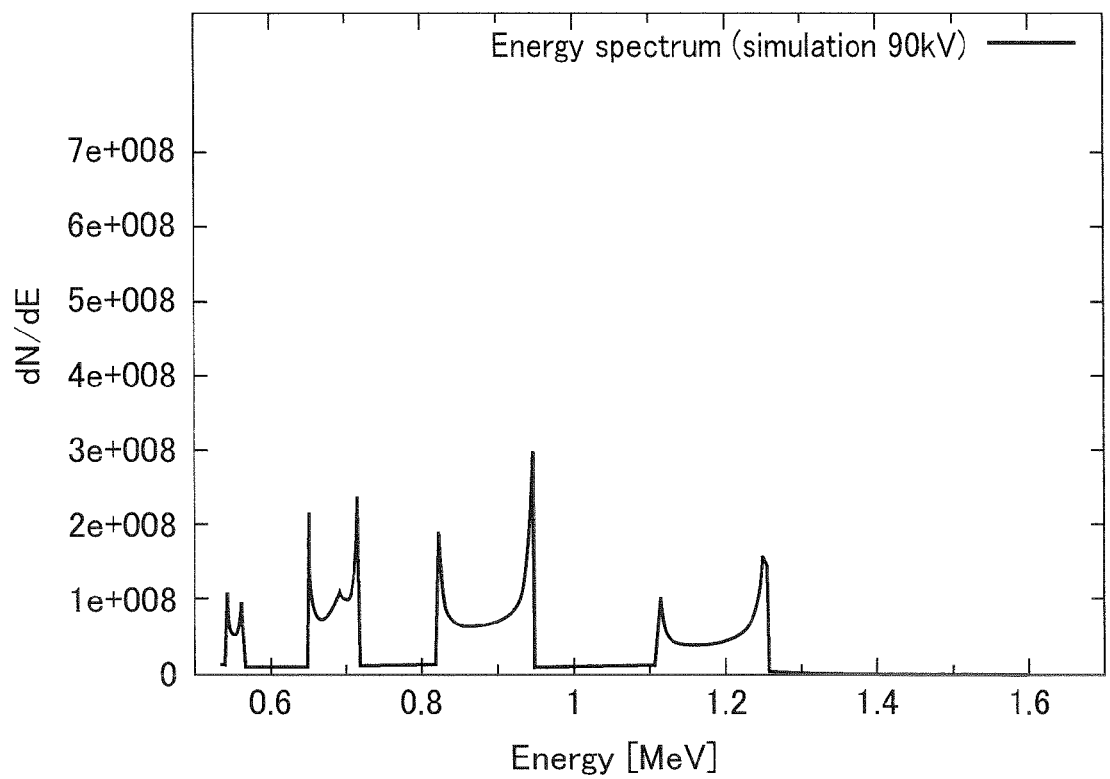
FIG. 7 is a diagram showing the energy spectrum of ion beams controlled with the ion beam control apparatus according to the first embodiment and the ion particle distribution in the radial direction based on prescribed energy (Case 3).
Figure 7B:
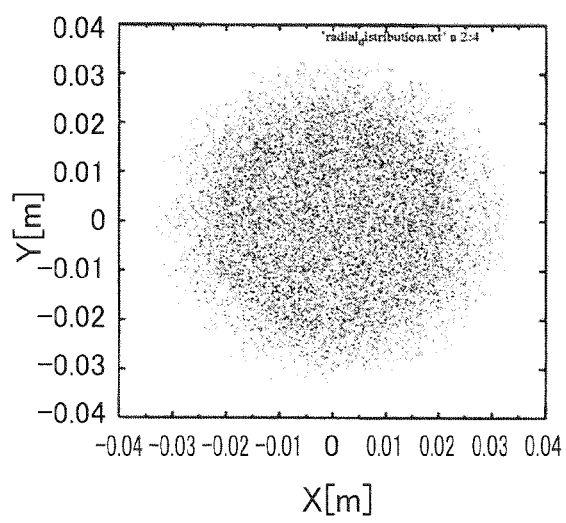
Figure 7C:
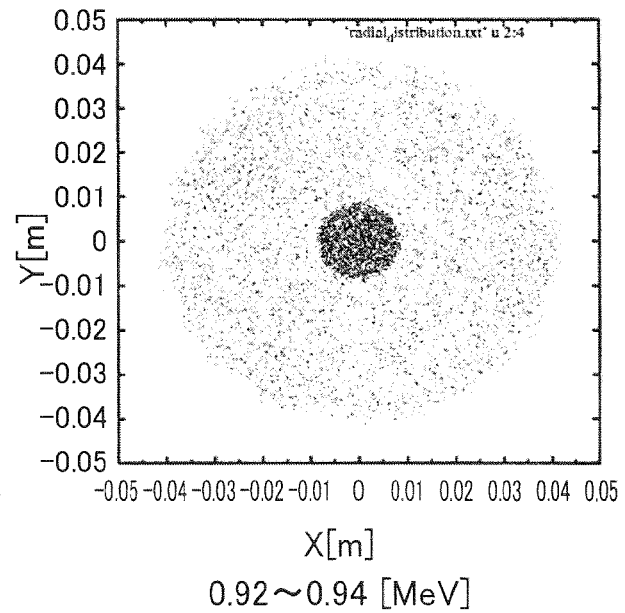

FIG. 3 is a diagram showing the relationship of the emission timing of the pulse laser beam and the phase of the radio frequency electric field. The upper row of FIG. 3 shows the time change of the strength of the electric field in the radio frequency electric field E(t), and the lower row thereof shows the entry timing of the ion beam IB. FIG. 4 is a diagram showing the test results and the simulation results. The solid line of FIG. 4 shows the test results, and the dashed line shows the simulation results. FIG. 5 to FIG. 7 are diagrams (Case 1 to Case 3) showing the energy spectrum of the ion beam controlled with the ion beam control apparatus in the first embodiment and the ion particle distribution in the moving radius direction based on prescribed energy. FIG. 5 shows a case where the voltage (amplitude) of the radio frequency electric field E(t) is 50 kV, FIG. 6 shows a case where the voltage (amplitude) of the radio frequency electric field E(t) is 80 kV, and FIG. 7 shows a case where the voltage (amplitude) of the radio frequency electric field E(t) is 90 kV. FIG. 5(A), FIG. 6(A) and FIG. 7(A) show the energy spectra, and the horizontal axis thereof shows the energy represented in MeV units, and the vertical axis thereof shows the intensity (existing probability). FIGS. 5(B), 5(C), FIGS. 6(B) to 6(G) and FIGS. 7(B), 7(C) show the ion particle distributions, and the horizontal axis and vertical axis thereof are respectively the X axis and the Y axis in cases where the traveling direction of the ion beam IB is the Z axis in an XYZ orthogonal coordinate system. FIG. 5(B) shows a case of 0.866 to 0.877 MeV, and FIG. 5(C) shows a case of 0.89 to 0.90 MeV. FIG. 6(B) shows a case of 0.65 to 0.68 MeV, FIG. 6(C) shows a case of 0.68 to 0.70 MeV, FIG. 6(D) shows a case of 0.70 to 0.72 MeV, FIG. 6(E) shows a case of 0.83 to 0.86 MeV, FIG. 6(F) shows a case of 0.86 to 0.89 MeV, and FIG. 6(G) shows a case of 0.89 to 0.92 MeV. FIG. 7(B) shows a case of 0.82 to 0.84 MeV, and FIG. 7(C) shows a case of 0.92 to 0.94 MeV.

The laser beam source 21 of the ion beam generation unit 2 emits the pulse laser beam PL having a pre-set prescribed pulse width at a pre-set prescribed cycle, and notifies this emission timing to the synchronization control unit 3. The pulse laser beam PL output from the laser beam source 21 is converged with the optical system 22 and irradiated onto the solid thin film 23 at a spot. When the pulse laser beam PL is irradiated onto the solid thin film 23, the solid thin film 23 is heated with the energy of the pulse laser beam PL, whereby the substance forming the solid thin film 23 and water and so on that are adsorbed on the solid thin film surface generate a plasma, and electrons (e$^-$) are foremost emitted. Induced by the electrons, protons (H$^+$) are subsequently emitted and fly to generate an ion beam IB of protons. Since the ion beam IB is generated based on the foregoing thermal process, the energy distribution of the ion beam IB will have a profile in which the intensity (existing probability of ions) will exponentially decrease according to the increase of energy in accordance with the Maxwell distribution as shown in FIG. 13(A). For example, if the pulse width of the pulse laser beam PL is approximately 50 to 100 fs, the temporal expansion of the ion beam IB at the time of being discharged from the solid thin film 23 will be in the order of picoseconds; for example, approximately 1 ps.

For instance, if the solid thin film 23 is configured from titanium, the solid thin film 23 will have a thickness of approximately 3 to 5 μm, and the pulse laser beam PL of approximately 3 to 4 TW will be irradiated onto the solid thin film 23 at a spot having a diameter of approximately 10 μm. Moreover, for example, if the solid thin film 23 is configured from tantalum, the solid thin film 23 will have a thickness of approximately 3 to 5 μm, and the pulse laser beam PL of approximately 3 to 4 TW will be irradiated onto the solid thin film 23 at a spot having a diameter of 10 μm. Further, for example, if the solid thin film 23 is configured from polyimide, the solid thin film 23 will have a thickness of approximately 7.5 μm, and the pulse laser beam PL of approximately 20 TW will be irradiated onto the solid thin film 23 at a spot having a diameter of 10 μm.

Incidentally, it has been reported that an ion beam IB of a substance forming the solid thin film 23; for instance, an ion beam IB of carbon ions can be generated by eliminating the water and so on that are adsorbed on the surface of the solid thin film 23 by heating the solid thin film 23 with a heat source such as a heater that generates heat.

The ion beam IB that is generated as described above is input to the ion beam control unit 1a. The input ion beam IB is input to the double gap radio frequency resonator 11a, and phase rotation by the radio frequency electric field E(t) is performed with the radio frequency electric field generation unit 112a.

More specifically, foremost, the input ion beam IB is input to the first gap G1 via the first electric field generation component 112a-1, and phase rotation by the radio frequency electric field E(t) is performed.

Here, the phase of the radio frequency electric field E(t) is synchronized with the input timing of the ion beam IB to the first gap G1 so that the ions of the ion beam IB having an energy that is higher than the energy corresponding to the intensity peak to be formed will be decelerated by being affected by the radio frequency electric field E(t), the ions of the ion beam IB having an energy corresponding to the intensity peak to be formed will not be affected by the radio frequency electric field E(t), and the ions of the ion beam IB having an energy that is lower than the energy corresponding to the intensity peak to be formed will be accelerated by being affected by the radio frequency electric field E(t). In this embodiment, as shown in FIG. 3, since the ions (protons) of the ion beam IB have a positive charge, if the positive direction of the radio frequency electric field E(t) is made to be the traveling direction of the ion beam IB (direction from the first electric field generation component 112a-1 to the second electric field generation component 112a-2), the phase of the radio frequency electric field E(t) is controlled so that the sine wave radio frequency electric field E(t) is switched from negative to positive at the timing that the ion beam IB passes through the center of the first gap G1. In order for the phase of the radio frequency electric field E(t) to be controlled as described above, the synchronization control unit 3 notifies the synchronization signal to the AC source 115a of the double gap radio frequency resonator 11a based on the notification of the emission timing from the laser beam source 21. If the ions of the ion beam IB are negative charge, the phase of the radio frequency electric field E(t) is controlled so that the sine wave radio frequency electric field E(t) is switched from positive to negative at the timing that the ion beam IB passes through the center of the first gap G1.

Moreover, if the vector representing the state of ions before being input to the first gap G1 (before the phase rotation) is Sb, and the vector representing the state of ions after being output from the first gap G1 (after the phase rotation) is Sa, this is represented as Sa=F·Sb, and the phase rotation matrix F of this formula is represented as shown in Formula 1 below.

$$\begin{pmatrix} 1 & 0 & 0 & 0 & 0 & 0 \\ k_r/(\beta\gamma)_f & (\beta\gamma)_i/(\beta\gamma)_f & 0 & 0 & 0 & 0 \\ 0 & 0 & 1 & 0 & 0 & 0 \\ 0 & 0 & k_r/(\beta\gamma)_f & (\beta\gamma)_i/(\beta\gamma)_f & 0 & 0 \\ 0 & 0 & 0 & 0 & 1 & 0 \\ 0 & 0 & 0 & 0 & k_z/(\beta\gamma)_f & (\beta\gamma)_i/(\beta\gamma)_f \end{pmatrix} \quad \text{Formula (1)}$$

Here, $k_r$ and $k_z$ are respectively represented as shown in Equation 2 and Equation 3 below.

$$k_r = -\frac{\pi q V_0 T g \sin\phi_s}{m_0 c^3 \bar{\beta}^2 \bar{\gamma}^2 f} \quad \text{Equation (2)}$$

$$k_z = \frac{2\pi q V_0 T g \sin\phi_s}{m_0 c^3 \bar{\beta}^2 \bar{\gamma}^2 f} \quad \text{Equation (3)}$$

Here, q represents the charge quantity of ions, $V_0$ represents the voltage to be applied to the gap G, T represents the transit time factor, g represents the spacing of the gap G, $\phi_s$ represents the phase of the radio frequency electric field E(t) upon ions of the ion beam IB having an energy corresponding to the intensity peak to be formed passing through the intermediate position of the gap, $m_0$ represents the mass of ions, c represents the luminous flux, β represents the value obtained by standardizing the ion velocity with the luminous flux (=(ion velocity)/(luminous flux)), γ represents the Lorents factor, and f represents the frequency of the radio frequency electric field E(t). The bar above the β and γ represents the average in the gaps. In this embodiment, q represents the charge quantity of protons, and $m_0$ represents the mass of protons.

When comparing the calculation (simulation) results (dashed line of FIG. 4) and the test results (solid line of FIG. 4) based on Equation 1 to Equation 3, as shown in FIG. 4, the simulation results are very similar to the test results, and Equation 1 to Equation 3 favorably represent the phase rotation by the radio frequency electric field E(t) that affects the ion beam IB.

The ion beam IB that was subject to phase rotation in the first gap G1 is input to the second gap G2 via the second electric field generation component 112a-2, and subject to phase rotation by the radio frequency electric field E(t). This phase rotation is represented with foregoing Equation 1 to Equation 3 as with the first gap G1.

Here, the spacing g of the first gap G1 and the length L of the second electric field generation component 112-2 are set as described above. Thus, the phase of the radio frequency electric field E(t) upon ions of the ion beam IB having an energy corresponding to the intensity peak to be formed passing through the intermediate position of the second gap G2 will be the same as the phase of the radio frequency electric field E(t) upon ions of the ion beam IB having an energy corresponding to the intensity peak to be formed passing through the intermediate position of the first gap G1. Thus, with the ion beam IB that is input to the second gap G2, the energy will be further compressed with the energy corresponding to the intensity peak to be formed based on the foregoing phase rotation by the radio frequency electric field E(t).

The ion beam IB that was subject to phase rotation by the double gap radio frequency resonator 11 is input to the collimator 12, and, with the input ion beam IB, ions having an energy corresponding to the intensity peak are sorted by the collimator 12, set to be a prescribed diameter, and then output.

More specifically, the ion beam IB input to the collimator 12 is foremost input to the magnetic field generation unit 121, the traveling direction (trajectory) of the respective ions of the ion beam IB is curved based on the magnetic field according to the momentum and, as shown in FIG. 2, spread in the trajectory b1 to b3 and fly toward the transmission blocking unit 122. The degree that the traveling direction is curved based on the magnetic field is small for ions with a large momentum (trajectory b1), and large for ions with a small momentum (trajectory b3). Thus, as a result of disposing the transmission blocking unit 122 so that the through-hole 1221 of the transmission blocking unit 122 is provided above the trajectory b2 of the ions having an energy corresponding to the intensity peak to be formed, only the ions having an energy corresponding to the intensity peak to be formed will be sorted, and output from the collimator 12. Moreover, as a result of setting the diameter of the through-hole 1221 to a prescribed size, the ion beam IB will be output from the collimator 12 with the prescribed diameter.

Based on the foregoing operation, the ion beam control apparatus Sa is able to control the energy expansion level and the size of the ion beam IB in the moving radius direction.

When simulating the energy spectra in the respective cases of 50 kV, 80 kV and 90 kV using Equation 1 to Equation 3, each energy spectrum will have multiple peaks (hereinafter referred to as the "global peaks") as respectively shown in FIG. 5(A), FIG. 6(A) and FIG. 7(A), and each peak will have a profile that is separated into two peaks (hereinafter referred to as the "local peaks"). During the simulation, the distance from the generation position of the ion beam IB (position that the solid thin film 23 is disposed) to the position that the ion beam IB is input to the first electric field generation component 112a-1 of the double gap radio frequency resonator 11a was set to 1 m. The frequency of the radio frequency electric field E(t) was set to the frequency of the master oscillator in the laser beam source 21 in the vicinity of 80 MHz, the length L of the second electric field generation component 112a-1 was set to 10 cm, and the first and second gaps G1, G2 were set to 2 cm.

For example, in a case where the voltage of the radio frequency electric field E(t) is 50 kV and the energy is 0.866 to 0.877 MeV, as shown in FIG. 5(B), the ion beam IB will be formed in a uniform diameter of approximately 0.06 m. Moreover, in a case where the voltage of the radio frequency electric field E(t) is 50 kV and the energy is 0.89 to 0.90 MeV, as shown in FIG. 5(C), the ion beam IB will be distributed within an area having a diameter of approximately 0.07 m, but a converging part having a diameter of approximately 0.04 m with high energy density can be seen in the center thereof. The case where the energy is 0.866 to 0.877 MeV and the case where the energy is 0.89 to 0.90 MeV both belong to the same global peaks, but even with these global peaks, depending on the energy, a converging part with high energy density will arise.

Moreover, in a case where the voltage of the radio frequency electric field E(t) is 80 kV and the energy is 0.65 to 0.68 MeV, as shown in FIG. 6(B), the ion beam IB shows a distribution having a uniform diameter of approximately 0.06 m. Moreover, in a case where the voltage of the radio frequency electric field E(t) is 80 kV and the energy is 0.68 to 0.70 MeV, as shown in FIG. 6(C), the ion beam IB shows a distribution having a diameter of approximately 0.08 m, but a converging part having a diameter of approximately 0.03 m with high energy density can be seen in the center thereof. Moreover, in a case where the voltage of the radio frequency electric field E(t) is 80 kV and the energy is 0.70 to 0.72 MeV, as shown in FIG. 6(D), the ion beam IB shows a distribution having a diameter of approximately 0.07 m, but a converging part having a diameter of approximately 0.02 m with high energy density can be seen in the center thereof. The case where the energy is 0.65 to 0.68 MeV and the case where the energy is 0.68 to 0.70 MeV and the case where the energy is 0.70 to 0.72 MeV belong to the same global peaks, but even with these global peaks, depending on the energy, a converging part with high energy density will arise. The tendency is that higher the energy, the higher the convergence level.

Moreover, in a case where the voltage of the radio frequency electric field E(t) is 80 kV and the energy is 0.83 to 0.86 MeV, as shown in FIG. 6(E), the ion beam IB shows a distribution having uniform energy density and a diameter of approximately 0.06 m. Moreover, in a case where the voltage of the radio frequency electric field E(t) is 80 kV and the energy is 0.86 to 0.89 MeV, as shown in FIG. 6(F), the ion beam IB shows a distribution having a diameter of approximately 0.08 m, but a converging part having a diameter of approximately 0.04 m with high energy density can be seen in the center thereof. Moreover, in a case where the voltage of the radio frequency electric field E(t) is 80 kV and the energy is 0.89 to 0.92 MeV, as shown in FIG. 6(G), the ion beam IB shows a distribution having a diameter of approximately 0.08 m, but a converging part having a diameter of approximately 0.03 m with high energy density can be seen in the center thereof. The case where the energy is 0.83 to 0.86 MeV and the case where the energy is 0.86 to 0.89 MeV and the case where the energy is 0.89 to 0.92 MeV belong to the same global peaks, but even with these global peaks, depending on the energy, a converging part with high energy density will arise. The tendency is that higher the energy, the higher the convergence level.

For example, in a case where the voltage of the radio frequency electric field E(t) is 90 kV and the energy is 0.82 to 0.84 MeV, as shown in FIG. 7(B), the ion beam IB shows a distribution having uniform energy density and a diameter of approximately 0.06 m. Moreover, in a case where the voltage of the radio frequency electric field E(t) is 90 kV and the energy is 0.92 to 0.94 MeV, as shown in FIG. 7(C), the ion beam IB shows a distribution having a diameter of approximately 0.08 m, but a converging part having a diameter of approximately 0.02 m with high energy density can be seen in the center thereof. The case where the energy is 0.82 to 0.84 MeV and the case where the energy is 0.92 to 0.94 MeV belong to the same global peaks, but even with these global peaks, depending on the energy, a converging part with high energy density will arise.

The reason why this kind of converging part arises is because the ions of the ion beam IB are a positive charge, and, when the sine wave radio frequency electric field E(t) is switched from positive to negative at the timing that the ion beam IB passes through the center position of the first gap G1, the electric line of force of the electric field E(t) that arises in the first gap G1 is a curve that is narrowed near the center of the first gap G1 as shown in FIG. 2. Consequently, a component of the electric field E(t) heading toward the center of the ion beam IB will arise in the traveling direction of the ion beam IB from one end of the first gap G1 to near the center of the gap G1, and the direction of the radio frequency electric field E(t) is reversed from near the center of the first gap G1 to the other end of the first gap G1. Thus, since a component of the electric field E(t) heading from the outside toward the center of the ion beam IB will arise, conversion will occur toward the center of the ion beam IB. The same applies to the second gap G2. In the foregoing case, the energy peak is not formed and will be of an expanding direction.

When using an ion beam IB having a relatively small diameter, an ion beam IB with higher energy density can be used by using an ion beam IB having a converging part instead of using an ion beam IB with uniform energy density by selectively extracting the converging party with the collimator 12 as a result of adjusting the diameter of the through-hole 1221 in the transmission blocking unit 122 of the collimator 12 to a smaller than the diameter of the converging part. For example, when using an ion beam IB having an energy of 086 to 0.9 MeV and a diameter of 0.04 m or less, the energy density will be higher when using an ion beam IB having a converging part and in which the energy is 0.89 to 0.90 MeV rather than using an ion beam IB having an energy of 0.866 to 0.877 MeV. Moreover, it is also possible to effectively generate an ion beam IB with high energy density by adjusting the diameter of the through-hole 1221 in the transmission blocking unit 122 of the collimator 12 to coincide with the diameter of the converging part.

The foregoing generation of the ion beam IB and the control of the ion beam IB are performed in a pre-set prescribed vacuum. Thus, for example, the ion beam control unit 1a and the ion beam generation unit 2 are housed in a vacuum chamber not shown, and air is evacuated with the vacuum pump to achieve the prescribed vacuum.

In the foregoing embodiment, the radio frequency resonator in the ion beam control unit 1a that causes the electric field to affect the ion beam IB and which performs phase rotation is configured from a double gap radio frequency resonator 11a including two gaps for forming the radio frequency electric field E(t). However, the foregoing radio frequency resonator may also be a single gap radio frequency resonator including one gap for forming the radio frequency electric field E(t), or a multiple gap radio frequency resonator including three or more gaps for forming the radio frequency electric field E(t). The ion beam control apparatus Sa comprising the foregoing types of radio frequency resonator is also able to control the energy expansion level of the ion beam and the size of the ion beam IB in the moving radius direction.

Another embodiment is now explained.

Second Embodiment

The radio frequency electric field E(t) that affects the ion beam IB has a certain limit due to an electrostatic breakdown, and, since two gaps were used to form the radio frequency electric field E(t) in the first embodiment, there was a limit in achieving the high energy of the ion beam IB. The ion beam control apparatus in the second embodiment uses three or more gaps to seek even higher energy of the ion beam IB. With the double gap radio frequency resonator 11a having two gaps, the ion beam IB is in a state where a converging part with high energy density exists and not in a state where the diameter in the radial direction is adjusted with the energy density being uniform as shown in FIG. 5 to FIG. 7. However, as a result of providing multiple gaps, as a result of shifting the phase of the radio frequency electric field E(t) in the adjacent gaps as large as 180 degrees, as described above, with the ion beam IB, the diameter in the radial direction will be adjusted with the energy density in a uniform state.

FIG. 8 is a diagram showing the configuration of the ion beam control unit in the second embodiment. FIG. 8(A) is a view showing a frame format of the configuration of the radio frequency electric field generation unit in the ion beam control unit, and FIG. 8(B) is a perspective view showing the configuration of the ion beam control unit.

The ion beam control apparatus Sb of the second embodiment comprises an ion beam control unit 1b, an ion beam generation unit 2, and a synchronization control unit 3. Specifically, the ion beam control apparatus Sb of the second embodiment uses the ion beam control unit 1b in substitute for the ion beam control unit 1a in the ion beam control apparatus Sa of the first embodiment. Thus, the explanation of the ion beam generation unit 2 and the synchronization control unit 3 is omitted.

The ion beam control unit 1b comprises, as shown in FIG. 8, a multiple gap radio frequency resonator 11b including multiple gaps to which an ion beam IB is input and which performs phase rotation by the radio frequency electric field E(t) for increasing the existing probability in the prescribed level of energy, and in which the phase of the radio frequency electric field E(t) in the adjacent gaps is shifted 180 degrees. In the example shown in FIG. 8, the multiple gap radio frequency resonator 11b (ion beam control unit 1b) comprises six gaps of first to sixth gaps G1 to G6.

In this embodiment, the multiple gap radio frequency resonator 11b comprises, for example, a cylindrical case 111b, a radio frequency electric field generation unit 112b (112b-1 to 112b-7) for generating the radio frequency electric field E(t), and a radio frequency (RF) AC source 115b.

The radio frequency electric field generation unit 112b comprises seven cylindrical first to seventh electric field generation component 112b-1 to 112b-7 arranged so the ion beam IB passes therethrough and the radio frequency electric field E(t) affects the ion beam IB. The first to seventh electric field generation components 112b-1 to 112b-7 are respectively arranged continuously from one side face to the other side face of the case 111b by being supported by rod-shaped first to seventh support members 113b-1 to 113b-7 that are suspended or effected at a prescribed spacing in the longitudinal direction from the inner face of the top cover of the case 111b so that they will mutually become a prescribed distance g of space, so that the central axis will mutually coincide, and so that the central axes of the first to seventh electric field generation components 112b-1 to 112b-7 and the central axis of the case 111b will mutually become orthogonal. This kind of resonator configured as described above is structured similar to a Wideröe-type resonator.

As a result of the radio frequency electric field generation unit 112b being configured as described above, a first space (first gap) G1 is formed between the first electric field generation component 112b-1 and the second electric field generation component 112b-2, a second space (second gap) G2 is formed between the second electric field generation component 112b-2 and the third electric field generation component 112b-3, a third space (third gap) G3 is formed between the third electric field generation component 112b-3 and the fourth electric field generation component 112b-4, a fourth space (fourth gap) G4 is formed between the fourth electric field generation component 112b-4 and the fifth electric field generation component 112b-5, a fifth space (fifth gap) G5 is formed between the fifth electric field generation component 112b-5 and the sixth electric field generation component 112b-6, and a sixth space (sixth gap) G6 is formed between the sixth electric field generation member 112b-6 and the seventh electric field generation component 112b-7.

With the electric field generation component 112b, in the example of the phase rotation cavity shown in FIG. 8(A), the length L of the second to sixth electric field generation components 112b-2 to 112b-6 is set so that (L+g) becomes equivalent to a value obtained by multiplying the ion velocity having an energy corresponding to the intensity peak to be formed to the even multiple time of a ½ cycle of the radio frequency electric field E(t). The first and seventh electric field generation components 112b-1, 112b-7 are components that are required for respectively forming the foregoing first space (first gap) and the foregoing sixth space (sixth gap), and may be of an arbitrary length.

When the length L of the second to sixth electric field generation components 112b-2 to 112b-6 is set as described above, the ions having an energy corresponding to the intensity peak to be formed will be affected by the phase rotation with a phase that differs 180 degrees (π radian) alternatively from the electric field E(t) of the first to sixth gaps G1 to G6. With a standard Wideröe-type resonator, the setting is such that the phases of the electric field E(t) upon the ions passing through the center position of the adjacent gaps G will be the same. In this embodiment, however, the multiple gap radio frequency resonator 11b differs in this respect, and with the multiple gap radio frequency resonator 11b of this embodiment, the phases of the electric field E(t) are set to change alternately 180 degrees upon the ions passing through the center position of the adjacent gaps G. As described later, the same applies to cases of adopting the structure of the Alvarez-type resonator to the multiple gap radio frequency resonator 11b.

The spacing g of the first to sixth gaps G1 to G6 is set, as with the first embodiment, to a distance which will not considerably change the phase of the radio frequency electric field E(t) when the ions having the energy corresponding to the intensity peak to be formed are flying between the gaps, and which enables the application of the required voltage without causing an electric breakdown.

The case 111, the electric field generation component 112b and the support component 114b are formed, for example, from a conductive material such as metal (including alloy), and, in this embodiment, for instance, is formed from copper from the perspective of conductive property, macinability and so on.

With the AC source 115b, one terminal thereof is connected to the case 111b, and the other terminal is disposed in the case 111b via a through-hole 114b that is drilled through the case 111b, and a radio frequency AC voltage is applied thereto. An insulating material is filled in the through-hole 114b, and the other terminal and the case 111b are insulated. A radio frequency electric field (E(t)) is thereby respectively generated in the first to sixth gaps G1 to G6 sequentially off by a half cycle. With the AC source 115b, the phase of the radio frequency electric field E(t) is controlled with a synchronization signal from the synchronization control unit 3.

Figure 9A:
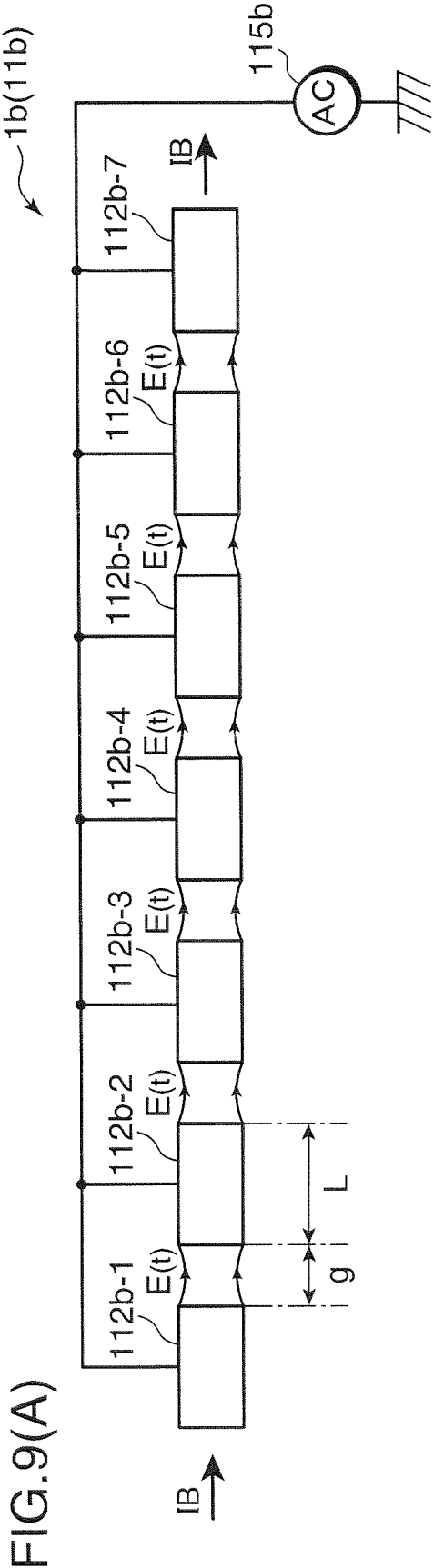
FIG. 9 is a diagram showing another configuration of an ion beam control unit according to the second embodiment.
Figure 9B:
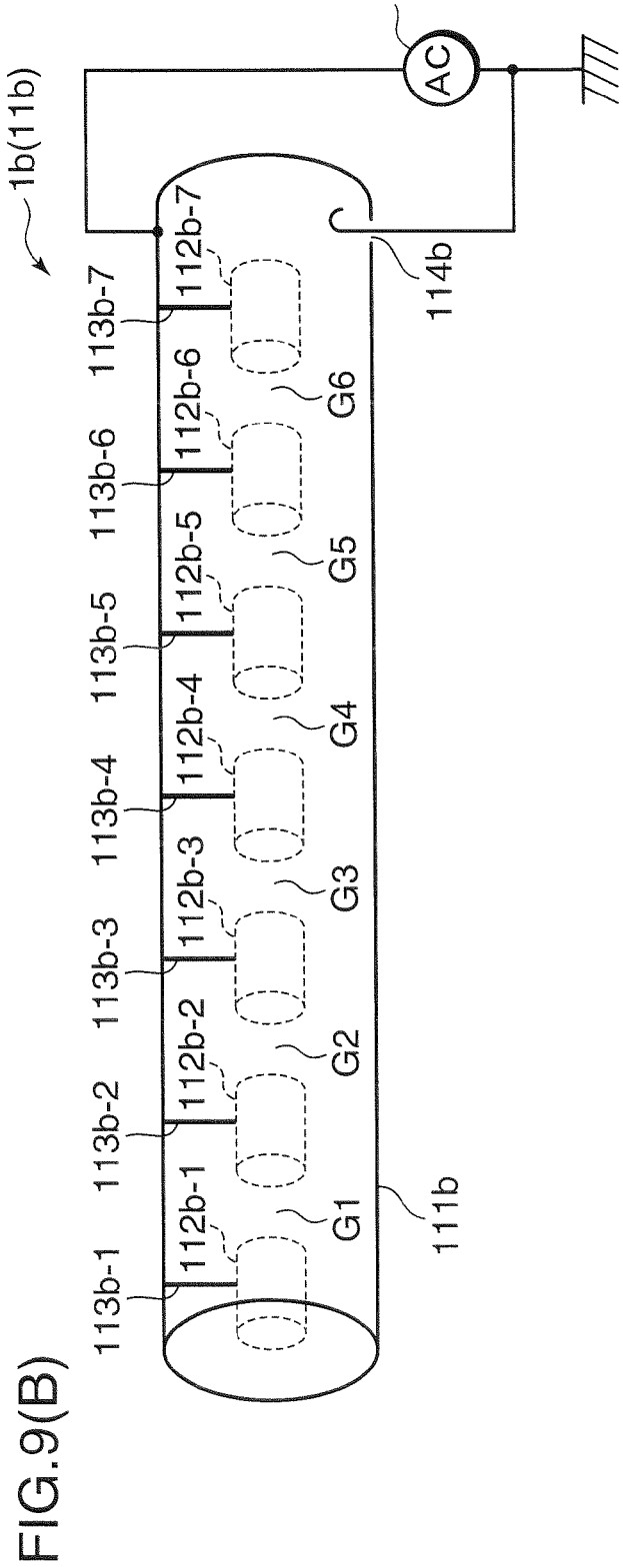

FIG. 9 is a diagram showing another configuration of the ion beam control unit in the second embodiment.

As the system of the resonator for forming the radio frequency electric field E(t), in addition to the above, for example, as shown in FIG. 9, the first to seventh electric field generation components 112b-1 to 112b-7 may all be resonators that are erected (or suspended) from the same direction by the first to seventh support components 113b-1 to 113b-7. This kind of resonator configured as described above is structured similar to the Alvarez-type resonator. In the case of a phase rotation cavity based on the Alvarez-type resonator structure, the length L of the second to sixth electric field generation components 112b-2 to 112b-6 is set so that (L+g) becomes equivalent to a value obtained by multiplying the ion velocity having an energy corresponding to the intensity peak to be formed to the odd multiple time of a ½ cycle of the radio frequency electric field E(t). With this kind of Alvarez-type resonator, the length L of the electric field generation component 112b can be shortened in comparison to the Wideröe-type resonator, and the resonator can be miniaturized.

The operation of the ion beam control apparatus Sb is now explained.

Figure 10A:
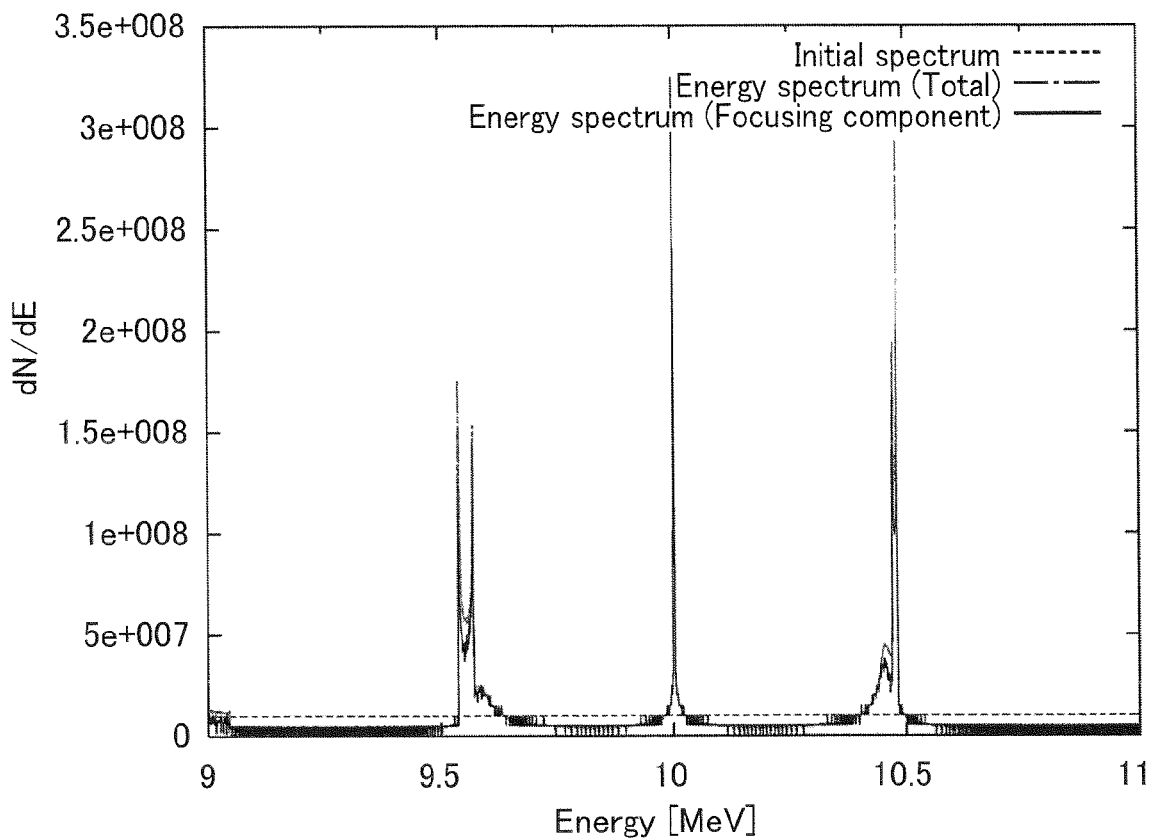
FIG. 10 is a diagram showing the energy spectrum of ion beams controlled with the ion beam control apparatus according to the second embodiment and the ion particle distribution in the radial direction based on prescribed energy.
Figure 10B:
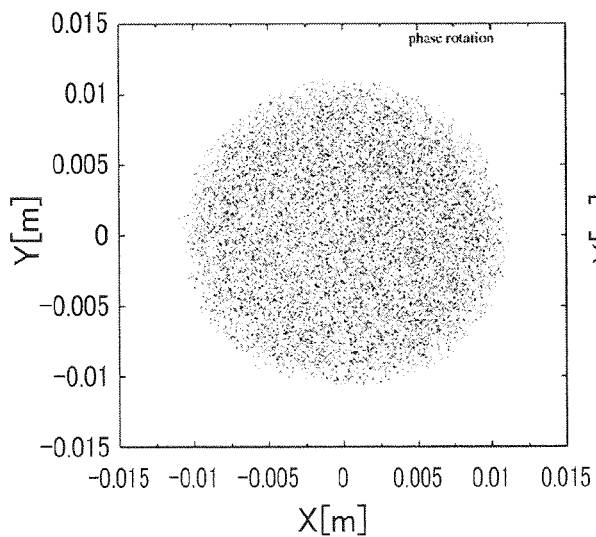
Figure 10C:
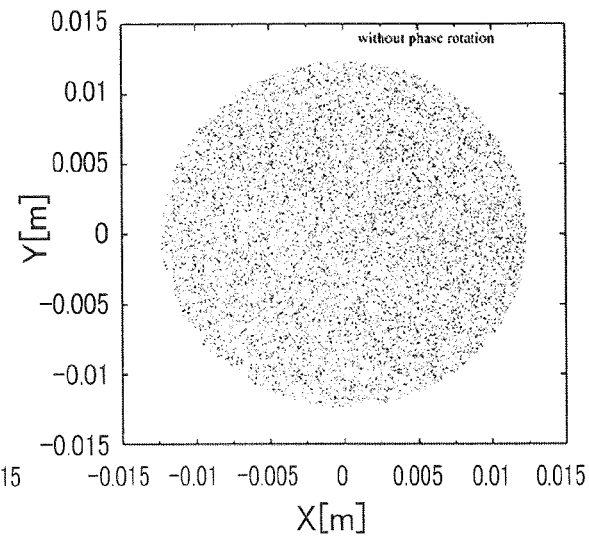
Figure 11A:
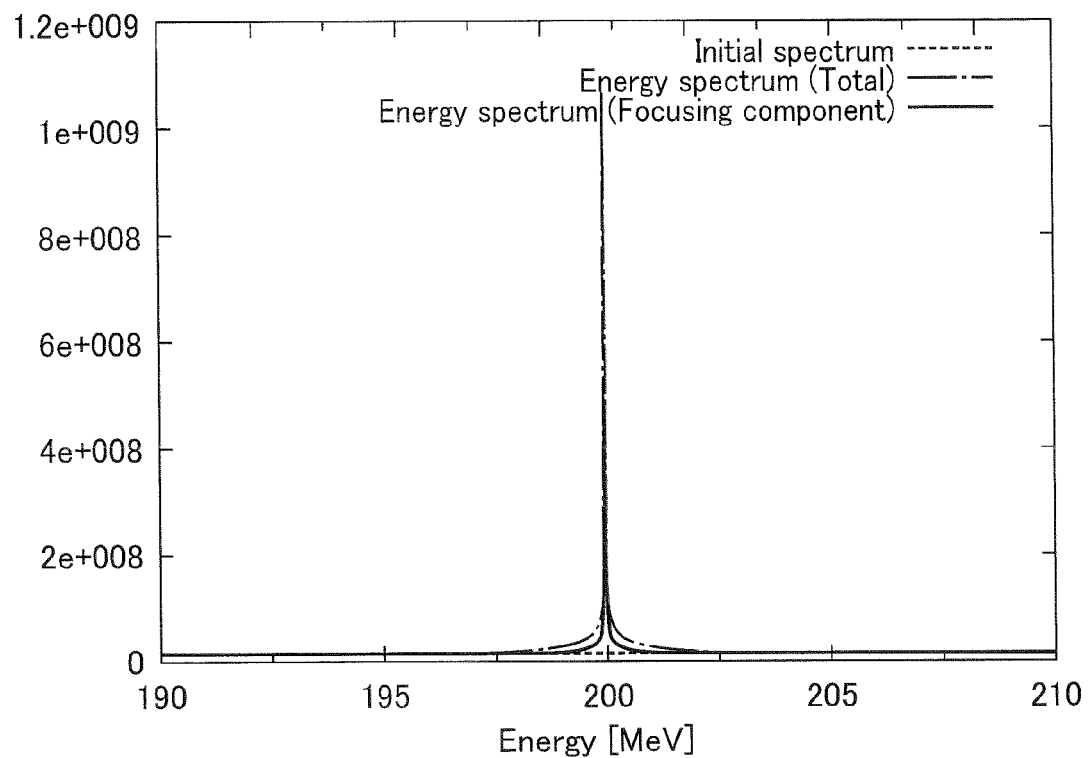
FIG. 11 is a comparative example, a diagram showing the energy spectrum of ion beams controlled with the ion beam control apparatus and the ion particle distribution in the radial direction based on prescribed energy.
Figure 11B:
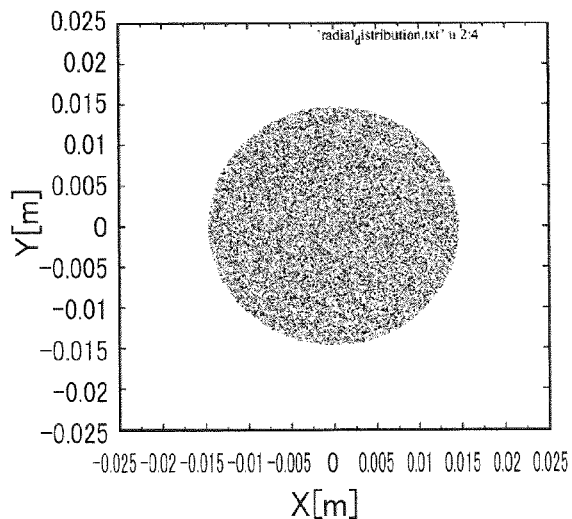
Figure 11C:
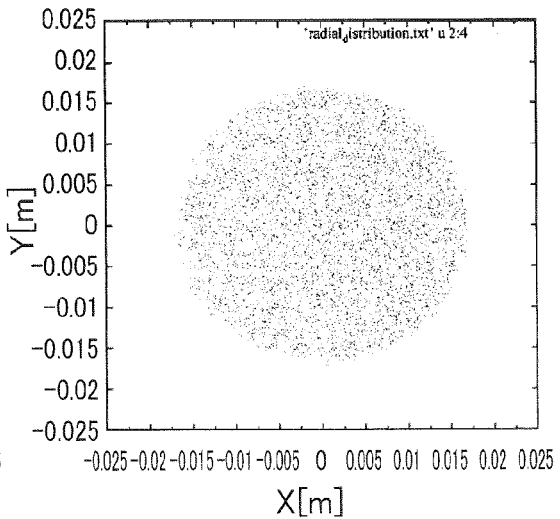
Figure 12:
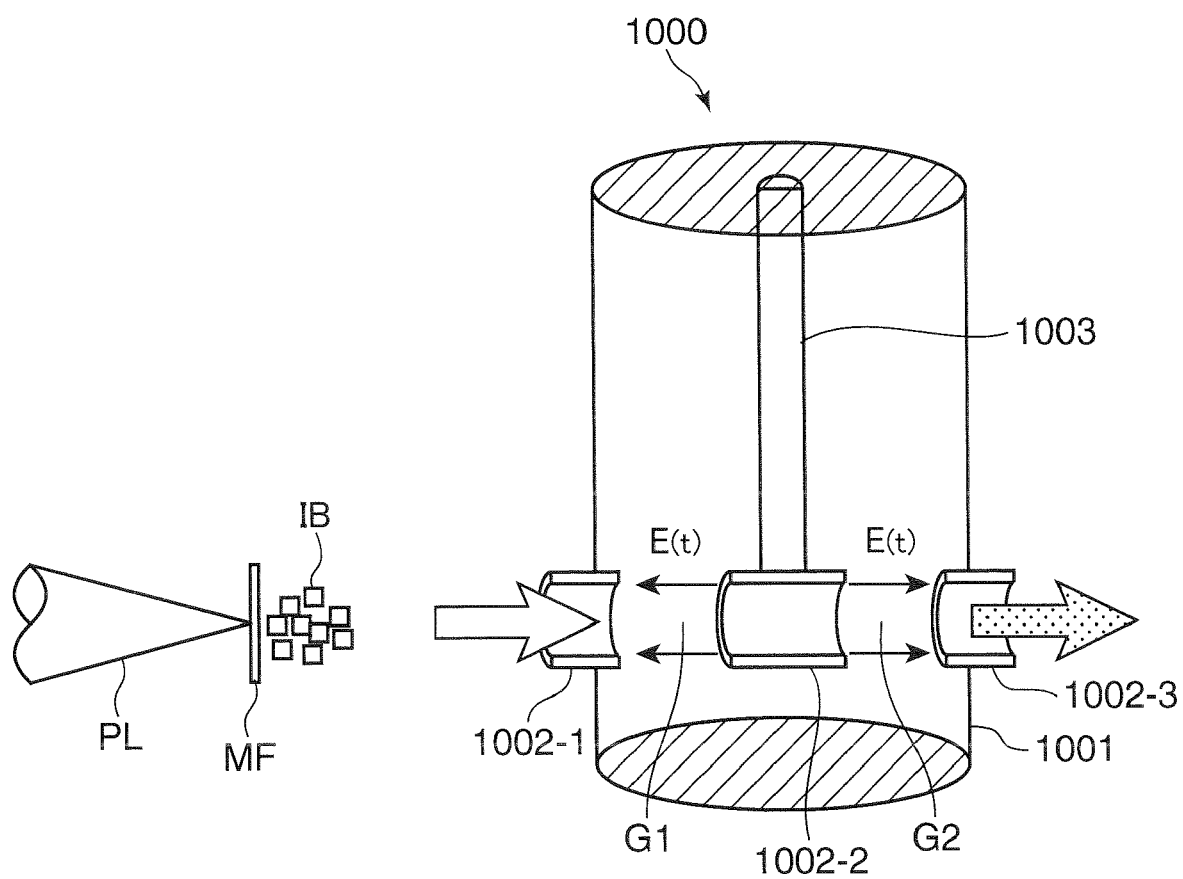
FIG. 12 is a diagram showing the configuration of a conventional ion beam control apparatus.
Figure 14:
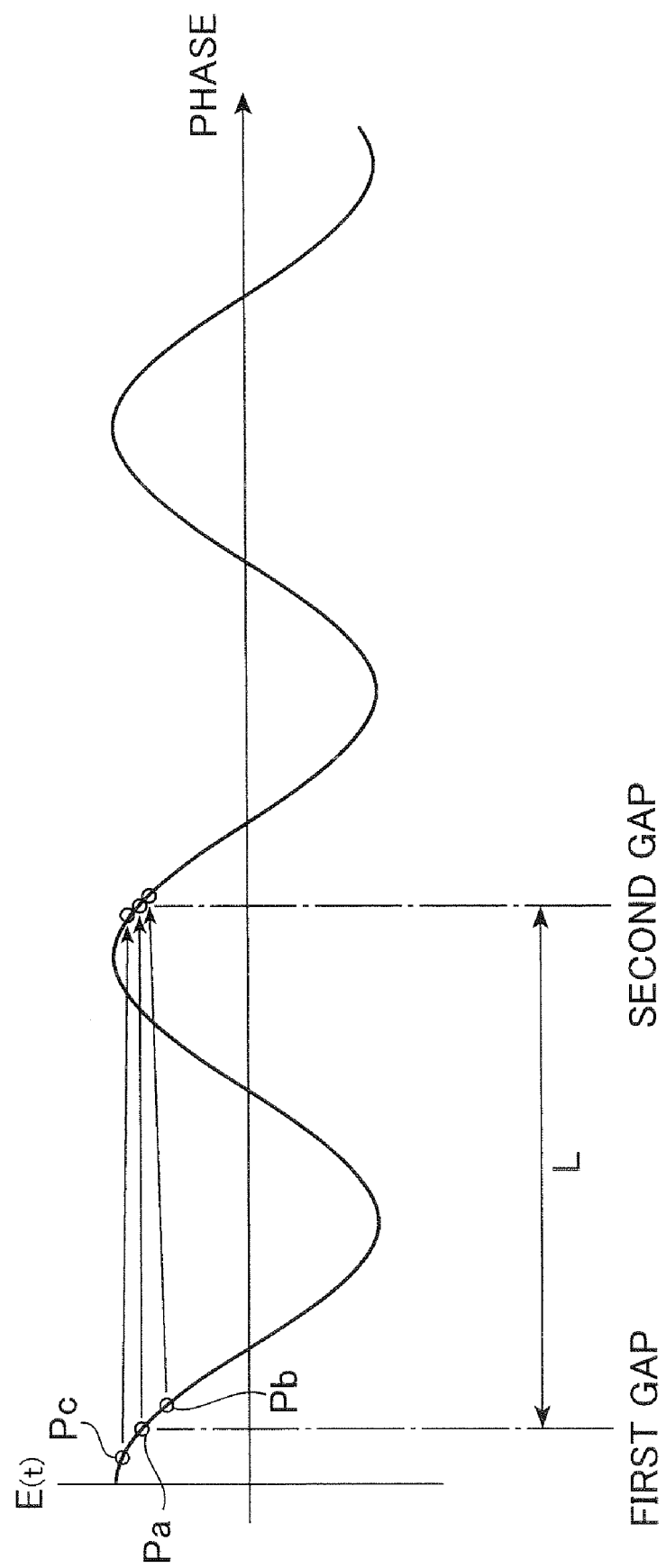
FIG. 14 is a diagram explaining the phase rotation of ion beams.

FIG. 10 is a diagram showing the energy spectrum of ion beams controlled with the ion beam control apparatus according to the second embodiment and the ion particle distribution in the radial direction based on prescribed energy. FIG. 11 is, as a comparative example, a diagram showing the energy spectrum of ion beams controlled with the ion beam control apparatus and the ion particle distribution in the radial direction based on prescribed energy. FIG. 11 differs from FIG. 10 only regarding the phase of the adjacent gaps G, and the phase of the adjacent gaps G is the same. FIG. 10(A) and FIG. 11(A) show the energy spectrum, and the horizontal axis thereof shows the energy represented in MeV units, and the vertical axis thereof shows the intensity (existing probability). FIGS. 10(B) and 10(C) as well as FIGS. 11(B) and 11(C) show the ion particle distribution, and the horizontal axis and vertical axis thereof are respectively the X axis and the Y axis in cases where the traveling direction of the ion beam IB is the Z axis in an XYZ orthogonal coordinate system. FIG. 10(B) and FIG. 11(C) show cases with phase rotation, and FIG. 10(C) and FIG. 11(B) shows cases without phase rotation.

The ion beam generation unit 2, as with the first embodiment, outputs the ion beam IB of protons (H+) by irradiating the pulse laser beam PL onto the solid thin film 23, and notifies the emission timing of the pulse laser beam PL to the synchronization control unit 3. The ion beam. IB output from the ion beam generation unit 2 is input to the ion beam control unit 1b. The input ion beam IB is input to the multiple gap radio frequency resonator 11b, and subject to phase rotation by the radio frequency electric field E(t) with the radio frequency electric field generation unit 112b.

More specifically, foremost, the input ion beam IB is input to the first gap G1 via the first electric field generation component 112b-1, and subject to phase rotation by the radio frequency electric field E(t).

Here, as with the first embodiment, the phase of the radio frequency electric field E(t) is synchronized with the input timing of the ion beam IB to the first gap G1 so that the ions of the ion beam IB having an energy that is higher than the energy corresponding to the intensity peak to be formed will decelerate by being affected by the radio frequency electric field E(t), the ions of the ion beam IB having an energy corresponding to the intensity peak to be formed will not be affected by the radio frequency electric field E(t), and the ions of the ion beam having an energy that is lower than the energy corresponding to the intensity peak to be formed will be accelerated by being affected by the radio frequency electric field E(t). In this embodiment, since the ions of the ion beam IB have a positive charge, the phase of the radio frequency electric field E(t) is controlled with a synchronization signal of the synchronization control unit 3 based on the emission timing of the pulse laser beam PL and which is also the synchronization signal of the synchronization control unit 3 notified to the AC source 115b so that the sine wave radio frequency electric field E(t) is switched from negative to positive at the timing that the ion beam IB passes through the center of the gap.

Subsequently, the ion beam IB subject to the phase rotation is input to the second gap G2 via the second electric field generation component 112b-2, and subject to phase rotation by the radio frequency electric field E(t). Subsequently, the ion beam IB subject to the phase rotation is input to the third gap G3 via the third electric field generation component 112b-3, and subject to phase rotation by the radio frequency electric field E(t). Subsequently, the ion beam IB subject to the phase rotation is input to the fourth gap G4 via the fourth electric field generation component 112b-4, and subject to phase rotation by the radio frequency electric field E(t). Subsequently, the ion beam IB subject to the phase rotation is input to the fifth gap G5 via the fifth electric field generation component 112b-5, and subject to phase rotation by the radio frequency electric field E(t). Subsequently, the ion beam IB subject to the phase rotation is input to the sixth gap G6 via the sixth electric field generation component 112b-6, and subject to phase rotation by the radio frequency electric field E(t). Then, the ion beam IB subject to the phase rotation is output from the seventh electric field generation component 112b-7, and output from the ion beam control unit 11b.

The ion beam IB input to the ion beam control unit 11b is sequentially subject to phase rotation by the radio frequency electric field E(t) in the first to sixth gaps G1 to G6 as described above. The phase rotation by the radio frequency electric field E(t) in the first to sixth gaps G1 to G6 is represented with foregoing Equation 1 to Equation 3 as with the first embodiment.

Here, the respective lengths L of the first to sixth gaps G1 to G6 and the second to sixth electric field generation components 112b-2 to 112b-6 are set as described above. Thus, when entering the ion beam IB into the gap G so that the ion beam IB passes through the center position of the gap G at the timing that the direction of the radio frequency electric field E(t) is switched from negative to positive, while the energy expansion of the ion beam IB is converged on the one hand, the size of the ion beam IB in the radial direction will expand. In the subsequent gap G, the ion beam IB will enter the gap G so that the ion beam IB will pass through the center position of the gap G at the timing that the direction of the radio frequency electric field E(t) is switched from positive to negative. In the foregoing case, while the energy expansion of the ion beam IB is dispersed on the one hand, the size of the ion beam IB in the moving radius direction will converge. Accordingly, the ion beam IB input to the first to sixth gaps G2 to G6 will be sequentially and repeatedly subject to the compression and decompression of energy with the energy corresponding to the intensity peak to be formed based on the phase rotation by the radio frequency electric field E(t), and the divergence and convergence of the size of the ion beam IB in the radial direction are sequentially repeated for each gap.

As a result of performing the foregoing operation, the ion beam control apparatus Sb is consequently able to control the energy expansion level of the ion beam and the size of the ion beam IB in the moving radius direction, and cause the ion beam IB to be of high energy.

From the perspective of achieving an even higher energy of the ion beam IB, there are cases where it would be more preferable to configure the ion beam control apparatus Sb where the ion beam IB enters the gap G so that the ion beam IB passes through the center position of the gap G at a timing that is off in comparison to the timing that the direction of the radio frequency electric field E(t) is switched from negative to positive.

Based on a simulation using Equation 1 to Equation 3, with the Alvarez-type resonator structure, as shown in FIG. 10(A), the energy spectrum will be a profile in which the energy has three peaks in the range of 9 MeV to 11 MeV; namely, in the vicinity of 9.6 MeV, in the vicinity of 10 MeV, and in the vicinity of 10.5 MeV. The peak in the vicinity of 9.6 MeV is formed of two local peaks, and the energy is approximately 17 times from $10^{+7}$ to approximately $1.7 \times 10^{+8}$. The peak in the vicinity of 10 MeV is formed of a single peak, and the energy is approximately 33 times from $10^{+7}$ to approximately $3.3 \times 10^{+8}$. And the peak in the vicinity of 10.5 MeV is formed of two local peaks, and the energy is approximately 30 times from $10^{+7}$ to approximately $3 \times 10^{+8}$. Moreover, as evident upon comparing FIG. 10(B) and FIG. 10(C), for instance, with the peak in the vicinity of 10 MeV, the diameter in the radial direction is smaller in the case of FIG. 10(B) (distribution of a diameter of approximately 0.022 m) that performs phase rotation by the radio frequency electric field E(t) in comparison to the case of FIG. 10(C) (distribution of a diameter of approximately 0.024 m) in which the energy density maintains a uniform state and the phase rotation by the radio frequency electric field E(t) is not performed.

Meanwhile, as the comparative example, if the setting is such that the ion beam IB passes through the center position of the respective gaps G constantly at the timing that the phase of the radio frequency electric field E(t) is converted from negative to positive without shifting the phase of the radio frequency electric field E(t) in the adjacent gaps G 180 degrees; that is, in cases where only energy compression is performed, as shown in FIG. 11, the diameter is diverged in the radial direction.

When the multiple gap radio frequency resonator 11b is designed to have an intensity peak at 200 MeV and simulation is performed with Equation 1 to Equation 3, with the Alvarez-type resonator structure, as shown in FIG. 11(A), the energy spectrum will have a profile in which the energy has a single peak in the range of 190 MeV to 210 MeV, and the peak energy is 100 times from $10^{+7}$ to $10^{+9}$. And as evident when comparing FIG. 11(B) and FIG. 11(C), the diameter in the radial direction is larger in the case of FIG. 11(C) (distribution of a diameter of approximately 0.032 m) that performs phase rotation by the radio frequency electric field E(t) in comparison to the case of FIG. 11(B) (distribution of a diameter of approximately 0.028 m) in which the energy density maintains a uniform state and the phase rotation by the radio frequency electric field E(t) is not performed.

During the simulation, the distance from the generation position of the ion beam IB (position that the solid thin film 23 is disposed) to the position that the ion beam IB is input to the first electric field generation component 112b-1 of the multiple gap radio frequency resonator 11b was set to 1 m. The frequency of the radio frequency electric field E(t) was set to 1.6 GHz, the length L of the second to sixth electric field generation components 112b-2 to 112b-6 was set to 8.62 cm, and the first to sixth gaps G1 to G6 were set to 2 cm.

This specification discloses various modes of technology as described above, and the main technology thereof can be summarized as follows.

One mode is directed to the ion beam control apparatus comprising an ion beam control unit for controlling an ion beam by at least using phase rotation by a radio frequency electric field that increases existing probability with a prescribed level of energy so that the ion beam is input, and the ion beam is output with a prescribed level of energy expansion and a prescribed diameter in a radial direction. Another mode is directed to the ion beam control method comprising a step of inputting an ion beam, a step of controlling an existing probability of the ion beam using phase rotation by a radio frequency electric field so as to increase the existing probability with a prescribed level of energy, and a step of controlling an energy expansion of the ion beam and a diameter in a radial direction so as to achieve the prescribed level of energy and a prescribed diameter in a radial direction.

With the ion beam control apparatus and ion beam control method configured as described above, the intensity peak is formed with the intended energy based on the phase rotation by the radio frequency electric field. Thus, the ion beam control apparatus and ion beam control method configured as described above are able to control the energy expansion level of the ion beam and the size of the ion beam in the radial direction by cutting out the intensity peak.

Preferably, the foregoing ion beam control apparatus includes a radio frequency resonator to which the ion beam is input and including a gap for performing phase rotation by the radio frequency electric field, and a collimator to which the ion beam output from the radio frequency resonator is input, and which outputs the input ion beam with the prescribed level of energy expansion and the prescribed diameter in the radial direction. One or multiple gaps can be provided.

With this kind of configuration, the radio frequency resonator forms the intensity peak with the intended energy, and the collimator cuts out the intensity peak. Consequently, the ion beam control apparatus having the foregoing configuration is able to control the energy expansion level of the ion beam IB and the size of the ion beam IB in the radial direction.

Preferably, the foregoing ion beam control apparatus comprises a multiple gap radio frequency resonator including multiple gaps to which the ion beam is input and which performs phase rotation by the radio frequency electric field, and in which the phase of the radio frequency electric field in the adjacent gaps is shifted 180 degrees.

With the foregoing configuration, the multiple gap radio frequency resonator repeats the phase rotation by the radio frequency electric field multiple times in order to increase the existing probability with the prescribed level of energy. Consequently, the ion beam control apparatus configured as described above is able to control the energy expansion level of the ion beam and the size of the ion beam in the radial direction. Moreover, since the phase rotation by the radio frequency electric field is repeated multiple times, it is possible to seek a higher energy of the ion beam.

Preferably, the foregoing ion beam control apparatus further comprises an ion beam generation unit for generating an ion beam to be input to the ion beam control unit. The ion beam generation unit is preferably an ion beam generation device using laser for generating an ion beam by irradiating a pulse laser beam on a solid thin film.

With the foregoing configuration, provided is an ion beam control apparatus further comprising an ion beam generation unit for generating ion beams, and there is no need to separately prepare an ion beam generation unit.

Preferably, with the foregoing ion beam control apparatus, the frequency of the radio frequency electric field is an integral multiple of a frequency of the pulse laser beam.

With the foregoing configuration, since the frequency of the radio frequency electric field is the frequency of the pulse laser beam, when controlling the phase of the radio frequency electric field and the timing of the pulse laser beam, such control can be facilitated. Thus, the control apparatus can be configured in a simple manner.

Preferably, the foregoing ion beam control apparatus further comprises a synchronization control unit for controlling the synchronization of the phase of the radio frequency electric field in the ion beam control unit and the generation timing of the ion beam in the ion beam generation unit so that the ion beam is input to the center position of the gap at the timing that the electric field direction is converted in the input direction of the ion beam.

With the foregoing configuration, since the synchronization control unit controls the synchronization, the ion beam formed with the radio frequency electric field is input to the center position of the gap at the timing that electric field direction is converted to the input direction of the ion beam. For example, if the ion beam is a beam of positive ions, the synchronization is controlled so that the ion beam is input to the center position of the gap at the timing that the electric field direction is converted from the reverse direction of the input direction of the ion beam to the foregoing input direction. The synchronization is controlled so that the ion beam is input to the center position of the gap at the conversion timing of the electric field direction according to the polarity of the ions in the ion beam. Thus, it is possible to efficiently increase the existing probability with the intended energy and increase the convergence level.

Preferably, the foregoing ion beam control apparatus includes an opening at a central part, wherein at least a pair of electrodes arranged to face each other is provided, an ion beam is input from a perpendicular direction of the opening, and, in a phase where an inclined part of a radio frequency electric field intensity accelerating or decelerating the ion beam to the pair of electrodes, the radio frequency is applied so as to cause the energy of the ion beam to focus on a specific energy and accelerate. With this ion beam control apparatus, at least another pair of electrodes arranged to face each other is provided to the pair of electrodes, and an ion beam is converged on the other pair of electrodes by an electric field component facing a beam center direction by applying radio frequency in a direction of accelerating the ions (main electric field vector is the same direction as the traveling direction of the ions) between an intermediate part of the other pair of electrodes and an electrode of an ion input side. Preferably, an ion beam is converged by an electric field component facing a beam center direction by applying radio frequency in a direction of decelerating the ions (main electric field vector is the reverse direction as the traveling direction of the ions) between the intermediate part of the other pair of electrodes and an electrode of an ion output side. More preferably, an ion beam is converged by an electric field component facing a beam center direction by applying radio frequency in a direction of accelerating the ions (main electric field vector is the same direction as the traveling direction of the ions) between an intermediate part of the pair of electrodes and an electrode of an ion input side, and, after the ion beam passes through the intermediate part of the electrode, an ion beam is converged by an electric field component facing a beam center direction by applying radio frequency in a direction of decelerating the ions (main electric field vector is the reverse direction as the traveling direction of the ions) between the intermediate part of the pair of electrodes and an electrode of an ion output side. More preferably, the pair of electrodes and the other pair of electrodes are arranged alternatively in multiple times.

With the foregoing configuration, it is possible to control the energy expansion level of the ion beam and the size of the ion beam in the radial direction.

Another mode is directed to the ion beam control method comprises a step of inputting an ion beam, and a step of repeating phase rotation by a radio frequency electric field that increases existing probability with a prescribed level of energy multiple times so as to achieve a prescribed level of energy expansion and a prescribed diameter in a radial direction.

With the foregoing configuration, the phase rotation by the radio frequency electric field is repeated multiple times for increasing the existing probability with the prescribed level of energy. Consequently, the ion beam control method configured as described above is able to control the energy expansion level of the ion beam and the size of the ion beam in the radial direction. In addition, since the phase rotation by the radio frequency electric field is repeated multiple times, it is possible to seek a higher energy of the ion beam.

The present invention was appropriately and sufficiently explained with the embodiments by referring to the drawings in order to express the invention. However, a person skilled in the art should be able to recognize that the foregoing embodiments can be easily changed and/or improved. Thus, so as long as the change or improvement made by the person skilled in the art is of a level that deviates from the scope of claims provided hereunder, such change or improvement shall be interpreted to be covered by said scope of claims.

The invention claimed is:

1. An ion beam control apparatus comprising an ion beam control unit for controlling an ion beam by at least using phase rotation by a radio frequency electric field that increases existing probability with a prescribed level of energy so that the ion beam is input and output with a prescribed level of energy expansion and a prescribed diameter in a radial direction.

2. The ion beam control apparatus according to claim 1, wherein the ion beam control unit comprises:
a radio frequency resonator to which the ion beam is input and which includes a gap for performing phase rotation by the radio frequency electric field; and
a collimator to which the ion beam output from the radio frequency resonator is input, and which outputs the input ion beam with the prescribed level of energy expansion and the prescribed diameter in the radial direction.

3. The ion beam control apparatus according to claim 2, further comprising a synchronization control unit for controlling synchronization of the phase of the radio frequency electric field in the ion beam control unit and generation timing of the ion beam in the ion beam generation unit so that the ion beam is input to the center position of the gap at timing that an electric field direction is converted in an input direction of the ion beam.

4. The ion beam control apparatus according to claim 1, wherein the ion beam control unit comprises:
a multiple gap radio frequency resonator including multiple gaps to which the ion beam is input, and which perform phase rotation by the radio frequency electric field, and in which the phase of the radio frequency electric field in the adjacent gaps is shifted 180 degrees.

5. The ion beam control apparatus according to claim 4, further comprising a synchronization control unit for controlling synchronization of the phase of the radio frequency electric field in the ion beam control unit and generation timing of the ion beam in the ion beam generation unit so that the ion beam is input to the center position of the gap at timing that an electric field direction is converted in an input direction of the ion beam.

6. The ion beam control apparatus according to claim 1, further comprising an ion beam generation unit for generating an ion beam to be input to the ion beam control unit.

7. The ion beam control apparatus according to claim 6, wherein the ion beam generation unit is an ion beam generation device using laser for generating an ion beam by irradiating a pulse laser beam on a solid thin film.

8. The ion beam control apparatus according to claim 7, wherein a frequency of the radio frequency electric field is an integral multiple of a frequency of the pulse laser beam.

9. An ion beam control method, comprising:
a step of inputting an ion beam;
a step of controlling an existing probability of the ion beam in use of phase rotation by a radio frequency electric field so as to increase the existing probability with a prescribed level of energy; and
a step of controlling an energy expansion of the ion beam and a diameter in a radial direction so as to achieve the prescribed level of energy and a prescribed diameter in a radial direction.

10. An ion beam control apparatus which includes an opening at a central part, and in which at least a pair of electrodes arranged to face each other is provided, an ion beam is input from a perpendicular direction of the opening, and in a phase where an inclined part having a radio frequency electric field intensity that accelerates or decelerates the ion beam, to the pair of electrodes the radio frequency is applied so as to cause the energy of the ion beam to focus on a specific energy for acceleration, wherein
at least another pair of electrodes arranged to face each other is provided with respect to the pair of electrodes, and
an ion beam is converged on the other pair of electrodes by an electric field component facing a beam center direction by applying radio frequency in a direction of accelerating the ions between an intermediate part of the other pair of electrodes and an electrode on an ion input side.

11. The ion beam control apparatus according to claim 10, wherein an ion beam is converged by an electric field component facing a beam center direction by applying a radio frequency in a direction of decelerating the ions between an intermediate part of the other pair of electrodes and an electrode on an ion output side.

12. The ion beam control apparatus according to claim 10, wherein an ion beam is converged by an electric field component facing a beam center direction by applying a radio frequency in a direction of accelerating the ions between an intermediate part of the pair of electrodes and an electrode on an ion input side, and, after the ion beam passes through the intermediate part of the electrode, the ion beam is converged by an electric field component facing a beam center direction by applying a radio frequency in a direction of decelerating the ions between the intermediate part of the pair of electrodes and an electrode on an ion output side.

13. The ion beam control apparatus according to claim 10, wherein the pair of electrodes and the other pair of electrodes are arranged multiple times facing each other.

14. An ion beam control method, comprising:
a step of inputting an ion beam; and
a step of repeating phase rotation by a radio frequency electric field that increases existing probability with a prescribed level of energy multiple times so as to achieve a prescribed level of energy expansion and a prescribed diameter in a radial direction.

* * * * *